US007241580B2

(12) United States Patent
Duellman et al.

(10) Patent No.: US 7,241,580 B2
(45) Date of Patent: Jul. 10, 2007

(54) IMMUNOAFFINITY CHROMATOGRAPHY USING EPITOPE TAGS TO POLYOL-RESPONSIVE MONOCLONAL ANTIBODIES

(75) Inventors: Sarah J. Duellman, Madison, WI (US); Nancy E. Thompson, Middleton, WI (US); Richard R. Burgess, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

(21) Appl. No.: 11/148,074

(22) Filed: Jun. 8, 2005

(65) Prior Publication Data

US 2005/0272919 A1     Dec. 8, 2005

Related U.S. Application Data

(60) Provisional application No. 60/577,944, filed on Jun. 8, 2004.

(51) Int. Cl.
| | | |
|---|---|---|
| G01N 33/53 | (2006.01) | |
| G01N 33/532 | (2006.01) | |
| C12P 21/00 | (2006.01) | |
| A61K 38/04 | (2006.01) | |
| A61K 38/08 | (2006.01) | |
| A61K 38/10 | (2006.01) | |
| C07K 1/10 | (2006.01) | |

(52) U.S. Cl. ............... 435/7.1; 435/69.1; 435/69.7; 436/544; 436/56; 530/300; 530/327; 530/328; 530/402; 536/23.4

(58) Field of Classification Search ............ 435/6, 435/7.1, 7.92, 69.1, 69.7; 436/544, 824, 436/56; 530/300, 350, 403, 412, 807, 327, 530/328, 402; 536/23.4
See application file for complete search history.

(56) References Cited

OTHER PUBLICATIONS

Corden et al. A unique structure at the carboxyl terminus of the largest subunit of eukaryotic RNA polymerase II. PNAS 1985, vol. 82, pp. 7934-79-38.*
Hisatake et al. Conserved structural motifs between Xenopus and human TFIIB. Nucleic Acids Research. 1991, vol. 19, p. 6639.*
Ing et al. Members of the steroid hormone receptor superfamily interact with TFIIB (S300-II). Journal of Biological Chemistry 1992, vol. 267, No. 25, pp. 17617-17623.*
L.C. Anthony, R.R. Burgess, Conformational flexibility in sigma70 region 2 during transcription initiation, *J. Biol. Chem.* 277 (2002) 46433-46441.
Anthony, L.C. Foley, K. Thompson, N. and Burgess R. R. Expression, purification of, and monoclonal antibodies to the sigma factors from E. coli. *Methods Enzymol.*, 370 (2003) 181-192.
T. M. Arthur, R. R. Burgess, Localization of a sigma 70 binding site on the terminus of the /Escherichia coli/ RNA polymerase b' subunit, *J. Biol. Chem.* 273 (1998) 31381-31387.

Bergendahl, V., Thompson, N.E., Foley, K., Olson, B., and Burgess, R.R. A cross-reactive polyol-responsive monoclonal antibody useful for isolation of core RNA polymerase from many bacterial species. *Protein Expression Purification*, 31(2003) 155-160.
R. R. Burgess, J. J. Jendrisak, A procedure for the rapid, large-scale purification of /Escherichia coli/ DNA-dependent RNA polymerase involving Polymin P precipitation and DNA-cellulose chromatography, *BIochemistry* 21 (1975) 4634-4638.
R. R. Burgess, T. M. Arthur, B. C. Pietz, Mapping protein-protein interaction domains using ordered fragment ladder far-western analysis of hexahistidine-tagged fusion proteins, *Methods Enzymol.* 328 (2000) 141-157.
R. R. Burgess, N.E. Thompson, Advances in gentle immunoaffinity chromatography, *Curr Opin. Biotechnol.* 13 (2002) 304-308.
M. Chalfie, Y. Tu, G. Euskirchen, W. W. Ward, D. C. Prasher, Green fluorescent protein as a marker for gene expression, *Science* 263 (1994) 802-805.
P. Cramer, D. A. Bushnell, J. Fu, A. L. Gnatt, B. Maier-Davis, N. E. THompson, R. R. Burgess, A. M. Edwards, P. R. David, R. D. Kornberg, Architecture of RNA polymerase II and implications for the transcription mechanism, *Science* 288 (2000) 640-649.
Duellman, s. j., thompson, n. e. and Burgess, R. R. An epitope tag derived from human transcription factor IIB (TFIIB) that reacts with a polyol-responsive monoclonal antibody. *Prot. Express Purific.* 35 (2004) 147-155.
A.M. Edwards, S.A. Darst, W.J. Feaver, N.E. Thompson, R.R. Burgess, R.D. Kornberg, Purification and lipid-layer crystallization of yeast RNA polymerase II, *Proc Natl Acad Sci USA* 87 (1990) 2122-2126.
Harlow E. and Lane D.: Antibodies: A Laboratory Manual. New York: Cold Spring Harbor Press, 1988.
Hill C. L., Bartholomew R., Beidler D., and David G.S., "Switch" immunoaffinity chromatography with monoclonal antibodies, *Biotechniques*, 1 (1983) 14-17.
J. W. Jarvik, C.A. Telmer, Epitope tagging, *Ann Rev Genet* 32 (1998) 601-618.

(Continued)

*Primary Examiner*—Long V. Le
*Assistant Examiner*—Shafiqul Haq
(74) *Attorney, Agent, or Firm*—Joseph T. Leone, Esq.; DeWitt Ross & Stevens S.C.

(57) ABSTRACT

Disclosed is a method of isolating, purifying, or concentrating a target compound. The method includes the steps of onjugating the target compound to an epitope for a polyol-responsive monoclonal antibody (PR-mAb) to yield a conjugate; and then contacting the conjugate to an immunoaffinity matrix comprising a PR-mAb specifically reactive with the PR-mAb epitope. Preferred epitopes for use in the method include amino acids of from 4 to about 30 amino acids, wherein the amino acid sequence comprises the sub-sequence D-X-S-R, (where X is any natural or unnatural amino acid), such as TKDPSRVG and TQDPSRVG. Additional epitopes for use in the method include SLAELLNGLGGS and PTSPSYSPTSPSYS. The method enables the rapid isolation of desired target compounds under gentle purification conditions.

29 Claims, 24 Drawing Sheets

OTHER PUBLICATIONS

J. J. Jendrisak, R. R. Burgess, A new method for the large-scale purification of wheat germ RNA polymerase II, *Biochemistry* 14 (1975) 4639-4645.

Y. Jiang, S.J. Zhang, S.M. Wu, M.Y. Lee, Immunoaffinity purification of DNA polymerase delta, *Arch Biochem Biophys* 320 (1995) 297-304.

Largaespada D.A., Jackson M. W., Thompson N. E., Kaehler D. A., Byrd L.G., and Mushinski J.F., The ABL-MYC retrovirus generates antigen-specific plasmacytomas by in vitro infection of activated B-lymphocytes from spleen and other murine lymphoid organs. *J Immunol Methods*, 197 (1996) 85-95.

N.A. Lynch, H. Jiang, D.T. Gibson, Rapid purification of the oxygenase component of toluene di-oxygenase from a polyol-responsive monoclonal antibody, *Appl Environ Microbiol* 62 (1996) 2133-37.

P.L. Nagy, J. Griesenbeck, R.D. Kornberg, M.L. Cleary, A trithorax-group complex purfied from /Saccharomyces cerevisiae/ is required for methylation of histone H3, *Proc Natl Acad Sci USA* 99 (2002) 90-94.

L. Rao, D. P. Jones, L. H. Nguyen, S. A. McMahan, R. R. Burgess, Epitope mapping using histidine-tagged protein fragments: application to /Escherichia coli/RNA polymerase sigma 70, *Anal. Biochem.* 241 (1996) 173-179.

Rhemrev-Boom M.M., Yates M, Rudolph M., and Raedts M., Immunoaffinity chromatography: a versatile tool for fast and selective purification, concentration, isolation and analysis, *J Pharm & Biomed Anal*, 24 (2001) 825-833.

A.B. Sparks, N.B. Adey, S. Cwirla, B.K. Kay, Screening phage-displayed random peptide libraries, in B.K. Kay, J. Winter, and J. McCafferty (Eds.) Phage Display of Peptides and Proteins, Academic Press, San Diego, CA, 1996, pp. 227-253.

F.W. Studier, A.H. Rosenberg, J.J. Dunn, J.W. Dubendorff, Use of T7 RNA polymerase to direct expression of cloned genes, *Meth Enzymol* 185 (1990) 60-89.

Subramanian A., Immunoaffinity chromatography, *Mol Biotechnol* 20 (2002) 41-47.

N.E. Thompson, D.B. Aronson, R.R. Burgess, Purification of eukaryotic RNA polymerase II by immunoaffinity chromatography. Elution of active enzyme with protein stabilizing agents from a polyol-responsive monoclonal antibody, *J Biol Chem* 265 (1990) 7069-7077.

N.E. Thompson, D.A. Hager, R.R. Burgess, Isolation and characterization of a polyol-responsive monoclonal antibody useful for gentle purification of /Escherichia/ / coli/ RNA polymerase, *Biochemistry* 31 (1992) 7003-7008.

N.E. Thompson, R.R. Burgess, Purification of recombinant human transcription factor IIB by immunoaffinity chromatography, *Protein Exp Purif* 5 (1994) 468-475.

N.E. Thompson, L.A. Strasheim, K.M. Nolan, R.R. Burgess, Accessibility of epitopes on human transcription factor IIB in the native protein and in a complex with DNA, *J Biol Chem* 270 (1995) 4735-4740.

N.E. Thompson, R.R. Burgess, Immunoaffinity purification of RNA polymerase II and transcription factors using polyol-responsive monoclonal antibodies, *Meth Enzymol* 274 (1996) 513-26.

N.E. Thompson, R.R. Burgess, Identification of polyol-responsive monoclonal antibodies for use in immunoaffinity chromatography, in: F.M. Ausubel et al. (Eds) Current protocols in molecular biology, vol. 2, John Wiley & Sons Inc., New York, 2001, pp. 11-18.1.

N.E. Thompson, T.M. Arthur, R.R. Burgess, Development of an epitope tag for the gentle purification of proteins by immunoaffinity chromatography: application to epitope-tagged green fluorescent protein, *Anal Biochem* 323 (2003) 171-179.

Thompson, N.E., Foley, K M, and Burgess, R.R. Antigen-binding properties of monoclonal antibodies reactive with human TATA-binding protein (TBP) and use in immunoaffinity chromatography. *Prot. Express. Purific.* In press, 2004.

R.Y. Tsien, The green fluorescent protein, *Ann Rev Biochem* 67 (1998) 509-544.

Velander W.H., Orthner C.L., Thatakan J.P., Madurawe R.D., Ralston A.H., Strickland D.K., and drohan W.N., Process implications for metal-dependent immunoaffinity interactions. *Biotechnol Prog*, 5 (1989) 119-125.

Weller, M.G., Immunochromatographic techniques—a critical review, *Fresenius J Anal Chem*, 366 (2000) 635-645.

See website for Ne clone, Inc., Madison, Wisconsin: www.neoclone.com <http://www.neoclone.com/>.

* cited by examiner

| | | | Length | Reactivity with NT73 |
|---|---|---|---|---|
| SEQ. ID. NO: 34 | APQVTAEDASASLAELLNAGLGGSDNE | (ep1) | 27 | YES |
| SEQ. ID. NO: 35 | ELLNAGLGGSDNE | (ep 2) | 13 | NO |
| SEQ. ID. NO: 36 | ASASLAELLNAG | (ep 3) | 12 | NO |
| SEQ. ID. NO: 37 | ASASLAELLNAGLGGSDNE | (ep 4) | 19 | YES |
| SEQ. ID. NO: 38 | SLAELLNAGLGGSDNE | (ep 5) | 16 | YES |
| SEQ. ID. NO: 39 | ASASLAELLNAGLGGS | (ep 6) | 16 | YES |

Positions: 1381 → APQVTAEDASASLAELLNAGLGGSDNE ← 1407

Tentative epitope:

| SEQ. ID. NO: 1 | SLAELLNAGLGGS | 13 | YES |
|---|---|---|---|

FIG. 11A

SEQUENCE LISTING

<160> NUMBER OF SEQ ID NOS: 39

<210> SEQ ID NO 1
<211> LENGTH: 12
<212> TYPE: PRT
<213> ORGANISM: Artificial
<220> FEATURE:
<223> OTHER INFORMATION: Isolated polyol-responsive epitope

<400> SEQUENCE: 1

Ser Leu Ala Glu Leu Leu Asn Gly Leu Gly Gly Ser
1               5                   10

<210> SEQ ID NO 2
<211> LENGTH: 14
<212> TYPE: PRT
<213> ORGANISM: Artificial
<220> FEATURE:
<223> OTHER INFORMATION: Isolated polyol-responsive epitope

<400> SEQUENCE: 2

Pro Thr Ser Pro Ser Tyr Ser Pro Thr Ser Pro Ser Tyr Ser
1               5                   10

<210> SEQ ID NO 3
<211> LENGTH: 8
<212> TYPE: PRT
<213> ORGANISM: Artificial
<220> FEATURE:
<223> OTHER INFORMATION: Isolated polyol-responsive epitope

<400> SEQUENCE: 3

Thr Lys Asp Pro Ser Arg Val Gly
1               5

<210> SEQ ID NO 4
<211> LENGTH: 8
<212> TYPE: PRT
<213> ORGANISM: Artificial
<220> FEATURE:
<223> OTHER INFORMATION: Isolated polyol-responsive epitope

<400> SEQUENCE: 4

Thr Gln Asp Pro Ser Arg Val Gly
1               5

<210> SEQ ID NO 5
<211> LENGTH: 4
<212> TYPE: PRT
<213> ORGANISM: Artificial
<220> FEATURE:
<223> OTHER INFORMATION: Polyol-responsive epitope tetrapeptide motif
<220> FEATURE:
<221> NAME/KEY: MISC_FEATURE
<222> LOCATION: (2)..(2)
<223> OTHER INFORMATION: Xaa can be any natural, unnatural, or modified
      amino acid

<400> SEQUENCE: 5

Asp Xaa Ser Arg
1

<210> SEQ ID NO 6
<211> LENGTH: 4
<212> TYPE: PRT
<213> ORGANISM: Artificial

```
<220> FEATURE:
<223> OTHER INFORMATION: Factor Xa protease recognition sequence
<220> FEATURE:
<221> NAME/KEY: MISC_FEATURE
<222> LOCATION: (2)..(2)
<223> OTHER INFORMATION: Xaa can be Glu or Asp

<400> SEQUENCE: 6

Ile Xaa Gly Arg
1

<210> SEQ ID NO 7
<211> LENGTH: 5
<212> TYPE: PRT
<213> ORGANISM: Artificial
<220> FEATURE:
<223> OTHER INFORMATION: Enterokinase protease recognition sequence

<400> SEQUENCE: 7

Asp Asp Asp Asp Lys
1               5

<210> SEQ ID NO 8
<211> LENGTH: 6
<212> TYPE: PRT
<213> ORGANISM: Artificial
<220> FEATURE:
<223> OTHER INFORMATION: Thrombin protease recognition sequence

<400> SEQUENCE: 8

Leu Val Pro Arg Gly Ser
1               5

<210> SEQ ID NO 9
<211> LENGTH: 7
<212> TYPE: PRT
<213> ORGANISM: Artificial
<220> FEATURE:
<223> OTHER INFORMATION: TEV protease recognition sequence

<400> SEQUENCE: 9

Glu Asn Leu Tyr Phe Gln Gly
1               5

<210> SEQ ID NO 10
<211> LENGTH: 8
<212> TYPE: PRT
<213> ORGANISM: Artificial
<220> FEATURE:
<223> OTHER INFORMATION: PreScission-brand protease recognition sequence

<400> SEQUENCE: 10

Leu Glu Val Leu Phe Gln Gly Pro
1               5

<210> SEQ ID NO 11
<211> LENGTH: 6
<212> TYPE: DNA
<213> ORGANISM: Escherichia coli

<400> SEQUENCE: 11 gaattc                                                              6

<210> SEQ ID NO 12
<211> LENGTH: 6
<212> TYPE: DNA
<213> ORGANISM: Bacillus amyloliquefaciens
```

```
<400> SEQUENCE: 12 ggatcc                                                              6

<210> SEQ ID NO 13
<211> LENGTH: 6
<212> TYPE: DNA
<213> ORGANISM: Haemophilus influenzae

<400> SEQUENCE: 13 aagctt                                                              6

<210> SEQ ID NO 14
<211> LENGTH: 7
<212> TYPE: DNA
<213> ORGANISM: Microcoleus sp.
<220> FEATURE:
<221> NAME/KEY: misc_feature
<222> LOCATION: (4)..(4)
<223> OTHER INFORMATION: n is a, c, g, or t

<400> SEQUENCE: 14 cctnagg                                                             7

<210> SEQ ID NO 15
<211> LENGTH: 4
<212> TYPE: DNA
<213> ORGANISM: Thermus aquaticus

<400> SEQUENCE: 15 tcga                                                                4

<210> SEQ ID NO 16
<211> LENGTH: 8
<212> TYPE: DNA
<213> ORGANISM: Nocardia otitidis

<400> SEQUENCE: 16 gcggccgc                                                            8

<210> SEQ ID NO 17
<211> LENGTH: 4
<212> TYPE: DNA
<213> ORGANISM: Arthrobacter luteus

<400> SEQUENCE: 17 agct                                                                4

<210> SEQ ID NO 18
<211> LENGTH: 10
<212> TYPE: PRT
<213> ORGANISM: Artificial
<220> FEATURE:
<223> OTHER INFORMATION: GFP/polyol-responsive epitope fusion peptide
      designated hIIB
<220> FEATURE:
<221> NAME/KEY: MISC_FEATURE
<222> LOCATION: (1)..(1)
<223> OTHER INFORMATION: The N-terminal G residue is fused to GFP.

<400> SEQUENCE: 18

Gly Ser Thr Lys Asp Pro Ser Arg Val Gly
1               5                   10

<210> SEQ ID NO 19
```

```
<211> LENGTH: 10
<212> TYPE: PRT
<213> ORGANISM: Artificial
<220> FEATURE:
<223> OTHER INFORMATION: GFP/polyol-responsive epitope fusion peptide
      designated hIIBK2Q
<220> FEATURE:
<221> NAME/KEY: MISC_FEATURE
<222> LOCATION: (1)..(1)
<223> OTHER INFORMATION: The N-terminal G residue is fused to GFP.

<400> SEQUENCE: 19

Gly Ser Thr Gln Asp Pro Ser Arg Val Gly
1               5                   10

<210> SEQ ID NO 20
<211> LENGTH: 10
<212> TYPE: PRT
<213> ORGANISM: Artificial
<220> FEATURE:
<223> OTHER INFORMATION: GFP/polyol-responsive epitope fusion peptide
      designated hIIBK2D
<220> FEATURE:
<221> NAME/KEY: MISC_FEATURE
<222> LOCATION: (1)..(1)
<223> OTHER INFORMATION: The N-terminal G residue is fused to GFP.

<400> SEQUENCE: 20

Gly Ser Thr Asp Asp Pro Ser Arg Val Gly
1               5                   10

<210> SEQ ID NO 21
<211> LENGTH: 11
<212> TYPE: PRT
<213> ORGANISM: Artificial
<220> FEATURE:
<223> OTHER INFORMATION: GFP/polyol-responsive epitope fusion peptide
      designated yIIB
<220> FEATURE:
<221> NAME/KEY: MISC_FEATURE
<222> LOCATION: (1)..(1)
<223> OTHER INFORMATION: The N-terminal G residue is fused to GFP.

<400> SEQUENCE: 21

Gly Ser Thr Gly Asp Asp Pro Ser Arg Val Gly
1               5                   10

<210> SEQ ID NO 22
<211> LENGTH: 14
<212> TYPE: PRT
<213> ORGANISM: Artificial
<220> FEATURE:
<223> OTHER INFORMATION: GFP/polyol-responsive epitope fusion peptide
<220> FEATURE:
<221> NAME/KEY: MISC_FEATURE
<222> LOCATION: (1)..(1)
<223> OTHER INFORMATION: The N-terminal G residue is fused to GFP.
<220> FEATURE:
<221> NAME/KEY: Epitope
<222> LOCATION: (2)..(14)
<223> OTHER INFORMATION: Polyol-responsive epitope

<400> SEQUENCE: 22

Gly Ser Leu Ala Glu Leu Leu Asn Ala Gly Leu Gly Gly Ser
1               5                   10

<210> SEQ ID NO 23
<211> LENGTH: 16
<212> TYPE: PRT
<213> ORGANISM: Artificial
<220> FEATURE:
```

```
<223> OTHER INFORMATION: GFP/polyol-responsive epitope fusion peptide
<220> FEATURE:
<221> NAME/KEY: MISC_FEATURE
<222> LOCATION: (1)..(1)
<223> OTHER INFORMATION: The C-terminal S residue is fused to GFP.
<220> FEATURE:
<221> NAME/KEY: Epitope
<222> LOCATION: (2)..(14)
<223> OTHER INFORMATION: Polyol-responsive epitope

<400> SEQUENCE: 23

Met Ser Leu Ala Glu Leu Leu Asn Ala Gly Leu Gly Gly Ser Gly Ser
1               5                   10                  15

<210> SEQ ID NO 24
<211> LENGTH: 8
<212> TYPE: PRT
<213> ORGANISM: Artificial
<220> FEATURE:
<223> OTHER INFORMATION: TFIIB polyol-responsive epitope

<400> SEQUENCE: 24

Thr Lys Asp Pro Ser Arg Val Gly
1               5

<210> SEQ ID NO 25
<211> LENGTH: 8
<212> TYPE: PRT
<213> ORGANISM: Artificial
<220> FEATURE:
<223> OTHER INFORMATION: hIIb polyol-responsive epitope

<400> SEQUENCE: 25

Thr Lys Asp Pro Ser Arg Val Gly
1               5

<210> SEQ ID NO 26
<211> LENGTH: 8
<212> TYPE: PRT
<213> ORGANISM: Artificial
<220> FEATURE:
<223> OTHER INFORMATION: hIIBK2Q polyol-responsive epitope

<400> SEQUENCE: 26

Thr Gln Asp Pro Ser Arg Val Gly
1               5

<210> SEQ ID NO 27
<211> LENGTH: 8
<212> TYPE: PRT
<213> ORGANISM: Artificial
<220> FEATURE:
<223> OTHER INFORMATION: hIIBK2D polyol-responsive epitope

<400> SEQUENCE: 27

Thr Asp Asp Pro Ser Arg Val Gly
1               5

<210> SEQ ID NO 28
<211> LENGTH: 9
<212> TYPE: PRT
<213> ORGANISM: Artificial
<220> FEATURE:
<223> OTHER INFORMATION: yIIB polyol-responsive epitope

<400> SEQUENCE: 28

Thr Gly Asp Asp Pro Ser Arg Val Gly
1               5
```

```
<210> SEQ ID NO 29
<211> LENGTH: 9
<212> TYPE: PRT
<213> ORGANISM: Artificial
<220> FEATURE:
<223> OTHER INFORMATION: Yeast TFIIB  polyol-responsive epitope

<400> SEQUENCE: 29

Thr Gly Asp Asp Pro Ser Arg Val Gly
1               5

<210> SEQ ID NO 30
<211> LENGTH: 36
<212> TYPE: PRT
<213> ORGANISM: Artificial
<220> FEATURE:
<223> OTHER INFORMATION: IIB8 epitope fragment

<400> SEQUENCE: 30

Gly Ser Glu Trp Arg Thr Phe Ser Asn Asp Lys Ala Thr Lys Asp Pro
1               5                   10                  15

Ser Arg Val Gly Asp Ser Gln Asn Pro Leu Leu Ser Asp Gly Asp Leu
            20                  25                  30

Ser Thr Met Ile
        35

<210> SEQ ID NO 31
<211> LENGTH: 10
<212> TYPE: PRT
<213> ORGANISM: Artificial
<220> FEATURE:
<223> OTHER INFORMATION: Poly-A sequence

<400> SEQUENCE: 31

Ala Ala Ala Ala Ala Ala Ala Ala Ala Ala
1               5                   10

<210> SEQ ID NO 32
<211> LENGTH: 40
<212> TYPE: PRT
<213> ORGANISM: Artificial
<220> FEATURE:
<223> OTHER INFORMATION: NT15 mAb epitope

<400> SEQUENCE: 32

Asp Arg Met Arg Arg Arg Ala Ala Gly Glu Ala Pro Ala Ala Pro Gln
1               5                   10                  15

Val Thr Ala Glu Asp Ala Ser Ala Ser Leu Ala Glu Leu Leu Asn Ala
            20                  25                  30

Gly Leu Gly Gly Ser Asp Asn Glu
        35                  40

<210> SEQ ID NO 33
<211> LENGTH: 27
<212> TYPE: PRT
<213> ORGANISM: Artificial
<220> FEATURE:
<223> OTHER INFORMATION: NT73 mAb epitope

<400> SEQUENCE: 33

Asp Arg Met Arg Arg Arg Ala Ala Gly Glu Ala Pro Ala Ala Pro Gln
1               5                   10                  15

Val Thr Ala Glu Asp Ala Ser Ala Ser Leu Ala
```

-continued 20              25

<210> SEQ ID NO 34
<211> LENGTH: 27
<212> TYPE: PRT
<213> ORGANISM: Artificial
<220> FEATURE:
<223> OTHER INFORMATION: mAb Nt73 epitope tag

<400> SEQUENCE: 34

Ala Pro Gln Val Thr Ala Glu Asp Ala Ser Ala Ser Leu Ala Glu Leu
1               5                   10                  15

Leu Asn Ala Gly Leu Gly Gly Ser Asp Asn Glu
            20                  25

<210> SEQ ID NO 35
<211> LENGTH: 13
<212> TYPE: PRT
<213> ORGANISM: Artificial
<220> FEATURE:
<223> OTHER INFORMATION: mAb Nt73 epitope tag

<400> SEQUENCE: 35

Glu Leu Leu Asn Ala Gly Leu Gly Gly Ser Asp Asn Glu
1               5                   10

<210> SEQ ID NO 36
<211> LENGTH: 12
<212> TYPE: PRT
<213> ORGANISM: Artificial
<220> FEATURE:
<223> OTHER INFORMATION: mAb Nt73 epitope tag

<400> SEQUENCE: 36

Ala Ser Ala Ser Leu Ala Glu Leu Leu Asn Ala Gly
1               5                   10

<210> SEQ ID NO 37
<211> LENGTH: 19
<212> TYPE: PRT
<213> ORGANISM: Artificial
<220> FEATURE:
<223> OTHER INFORMATION: mAb Nt73 epitope tag

<400> SEQUENCE: 37

Ala Ser Ala Ser Leu Ala Glu Leu Leu Asn Ala Gly Leu Gly Gly Ser
1               5                   10                  15

Asp Asn Glu

<210> SEQ ID NO 38
<211> LENGTH: 16
<212> TYPE: PRT
<213> ORGANISM: Artificial
<220> FEATURE:
<223> OTHER INFORMATION: mAb Nt73 epitope tag

<400> SEQUENCE: 38

Ser Leu Ala Glu Leu Leu Asn Ala Gly Leu Gly Gly Ser Asp Asn Glu
1               5                   10                  15

<210> SEQ ID NO 39
<211> LENGTH: 16
<212> TYPE: PRT
<213> ORGANISM: Artificial
<220> FEATURE:
<223> OTHER INFORMATION: mAb Nt73 epitope tag

```
<400> SEQUENCE: 39

Ala Ser Ala Ser Leu Ala Glu Leu Leu Asn Ala Gly Leu Gly Gly Ser
1               5                   10                  15
```

IMMUNOAFFINITY CHROMATOGRAPHY USING EPITOPE TAGS TO POLYOL-RESPONSIVE MONOCLONAL ANTIBODIES

CROSS-REFERENCE TO RELATED APPLICATIONS

Priority is hereby claimed to provisional application Ser. No. 60/577,944, filed Jun. 8, 2004, the entire content of which is incorporated herein.

FEDERAL FUNDING

This work was made with United States government support awarded by the following agencies: NIH CA060896. United States has certain rights in this invention.

INCORPORATION BY REFERENCE

All of the papers cited in the Bibliography are incorporated herein by reference.

BACKGROUND

Immunoaffinity chromatography is a valuable protein separation technique that takes advantage of the binding specificity between an antibody and its antigen. (For a review see reference [1].) This purification method, however, is inherently limited due to the tight binding between the antibody and its antigen. In a great many instances, a high concentration of denaturing reagents, or extreme pH values, or both, is required to dissociate the antibody-antigen complex. As a result, the process of dissociating the antibody from its antigen often yields a denatured protein product. Where the antigen to be isolated is a multi-subunit protein complex, these concerns are more troublesome because the conditions must be sufficiently harsh to dissociate the antibody-antigen complex, but not so harsh as to dissociate the protein complex itself.

The term "immunoaffinity chromatography" as used herein designates any method that uses immobilized antibodies in affinity chromatography. Immunoaffinity chromatography is one of the most powerful protein purification procedures currently available. When successfully executed, the exquisite specificity and high affinity of the antibody-antigen interaction lead to the highly selective absorption of target proteins to the immobilized antibodies. Thus, by applying a protein mixture to a suitable antibody immobilized on a resin, washing off unbound or weakly bound material, and then eluting the antigenic protein with appropriate elution agents, both purification (often of greater than 1,000-fold) and simultaneous concentration can be achieved. As a result, immunoaffinity chromatography has proven extremely useful for both biochemical laboratory-scale and large-scale protein purification [18, 19, 20].

Two types of antibodies are used in immunoaffinity chromatography, polyclonal antibodies and monoclonal antibodies. On one hand, polyclonal antibodies, obtained by immunizing a rabbit or goat and purifying the immunoglobulin fraction from the resulting serum, are mixtures of antibodies with a variety of specificities and binding properties. Polyclonal antibodies are capable of binding to various parts (epitopes) of the protein used as the immunogen. Polyclonal antibodies are relatively easy to produce but suffer from several disadvantages when used in immunoaffinity chromatography. Most notably, polyclonal antibodies are heterogeneous with respect to epitope specificity and binding properties. Therefore, great care must be taken to immunize the animal with highly pure protein to avoid raising unwanted antibodies to minor impurities in the inoculation preparation. Also, the antibody preparation is not completely reproducible from one immunized animal to another. (Each animal has a similar but not identical immune response to the inoculant.) This makes it impossible to obtain large quantities of antibodies with consistent properties.

On the other hand, monoclonal antibodies, while more difficult and expensive to produce than polyclonal antibodies, have several advantages for use in immunoaffinity chromatography. Monoclonal antibodies can be produced with smaller quantities of less purified immunogen. Once a hybridoma line is established, it can be used to produce a potentially unlimited supply of antibody with reproducible properties. Most importantly, the antibody binds to a single epitope on the antigen and thus has homogeneous binding and dissociation (i.e., elution) properties.

As noted earlier, because of the strength of the antigen-antibody interaction, it is usually difficult to elute the antigen from an immunoaffinity column. It is not uncommon to employ quite harsh elution conditions, such as extreme pH values (pH 3 or 10), denaturing agents (8 M urea or 6 M guanidinium hydrochloride), or chaotropic salts (3 M KSCN) that disrupt protein structure. The elution conditions often damage labile proteins, especially multi-subunit enzymes, resulting in very low yields of active, purified protein. The harsh conditions also decrease the lifetime of the antibody column.

Monoclonal antibodies with a variety of special properties have been isolated in an effort to avoid the requirements of harsh elution conditions. In a very early study, monoclonal antibodies were screened for those that required less extreme pH's for elution of the antigen; e.g., elution at pH 4.5 instead of pH 3 [21]. Monoclonal antibodies were also found that bind to antigen in the presence of $Ca^{+2}$ and can be eluted with the calcium chelator EGTA [22].

A specific sub-type of monoclonal antibody, called a "polyol-responsive" monoclonal antibody (hereinafter "PR-mAb") has properties that are ideally suited for use in immunoaffinity chromatography. A PR-mAb binds very tightly to its antigen under many standard conditions, but releases the antigen when eluted under very mild, non-denaturing conditions, namely an aqueous buffer at neutral pH supplemented with a low molecular-weight polyhydroxylated compound (i.e., a polyol), such as ethylene glycol or propylene glycol, and a nonchaotropic salt such as NaCl or ammonium sulfate. Generally salt alone or polyol alone do not cause antigen elution, although some mAbs respond to polyol alone. The resulting purified proteins are active and multi-subunit complexes are retained. (For reviews see [2, 3, and 4].) PR-mAb immunoaffinity chromatography has been used successfully to purify large multi-protein complexes such as RNA polymerase (RNAP) [5, 6, 7].

Six different PR-mAbs have been employed in immunoaffinity chromatography in the lab of the present inventors [3, 4]. The PR-mAb identification procedure set forth in reference [4] has also been used in other labs to isolate PR-mAbs for gently purifying a variety of proteins and protein complexes [8, 9, 10]. However, PR-mAbs make up only about 5% to perhaps 10% of the antibody repertoire in the mouse [7]. Moreover, there are far more proteins to be isolated than there are corresponding PR-mAbs. Thus, there remains a long-felt and unmet need to expand the range of protein targets that can be purified by immunoaffinity chromatography using PR-mAbs.

SUMMARY OF THE INVENTION

A first embodiment of the invention is directed to a method of isolating, purifying, or concentrating a target compound. The method comprises conjugating the target compound to an epitope for a polyol-responsive monoclonal antibody (PR-mAb), thereby to yield a conjugate. The conjugate is then contacted to an immunoaffinity matrix comprising a PR-mAb specifically reactive with the PR-mAB epitope. In this fashion, the conjugates (which comprise the target compound) are immobilized on the immunoaffinity matrix. Non-target compound impurities are then rinsed from the column. The conjugates can then be released from the matrix by treating it with a polyol.

The target compound can be conjugated to the epitope via a linker, or the target compound can be conjugated directly to the epitope, without an intervening linker. When a linker is present, it is preferred that the linker is thermolabile, chemically labile, chemically cleavable, or a recognition/cleavage site for an enzyme (e.g., a recognition and/or cleavage site for a peptidase, protease or a restriction endonuclease).

In the most preferred embodiment, the target compound is conjugated to an epitope selected from the group consisting of SLAELLNGLGGS (SEQ. ID. NO: 1), PTSPSYSPTSPSYS (SEQ. ID. NO: 2), TKDPSRVG (SEQ. ID. NO: 3), and TQDPSRVG (SEQ. ID. NO: 4). It is generally preferred that the target compound is conjugated to an epitope selected from the group consisting of an amino acid of from 4 to about 30 amino acids, wherein the amino acid sequence comprises the sub-sequence D-X-S-R (SEQ. ID. NO: 5), wherein X is any natural or unnatural amino acid.

Another embodiment of the invention is a method of isolating, purifying, or concentrating a target polypeptide or protein, as in the first embodiment. However, in this second embodiment, the method comprises providing a fusion protein comprising the target polypeptide or protein and an epitope for a PR-mAb. The fusion protein is then contacted to an immunoaffinity matrix comprising a PR-mAb specifically reactive with the PR-mAB epitope. As in the first embodiment, the fusion protein can include a linker interspersed between target compound and the epitope. Or the target compound can be bonded directly to the epitope (without an intervening linker) within the fusion protein. When a linker is present, it is preferred that the linker is thermolabile, chemically labile, chemically cleavable, or a recognition/cleavage site for an enzyme.

Yet another embodiment of the invention is a method of isolating, purifying, or concentrating a target compound. Here, the method comprises conjugating a probe compound capable of binding to the target compound to an epitope for a polyol-responsive monoclonal antibody (PR-mAb) to yield a conjugate. The conjugate is then contacted to a sample suspected of containing the target compound under conditions and for a time sufficient to allow the test compound to bind to the probe, thereby yielding a probe/target mixture. The probe/target mixture is then contacted to an immunoaffinity matrix comprising a PR-mAb specifically reactive with the PR-mAb epitope.

The invention is also directed to a composition of matter comprising a target compound conjugated to an isolated polypeptide having an amino acid sequence selected from the group consisting of SLAELLNGLGGS (SEQ. ID. NO: 1), PTSPSYSPTSPSYS (SEQ. ID. NO: 2), TKDPSRVG (SEQ. ID. NO: 3), and TQDPSRVG (SEQ. ID. NO: 4).

The invention is further directed to a composition of matter comprising: a target compound, a linker, and an isolated polypeptide, wherein the target compound is conjugated to the linker, and the linker is conjugated to the isolated polypeptide, and the further wherein the isolated polypeptide has an amino acid sequence selected from the group consisting of SLAELLNGLGGS (SEQ. ID. NO: 1), PTSPSYSPTSPSYS (SEQ. ID. NO: 2), TKDPSRVG (SEQ. ID. NO: 3), and TQDPSRVG (SEQ. ID. NO: 4).

Yet another embodiment of the invention is an isolated polypeptide having an amino acid sequence selected from the group consisting of SLAELLNGLGGS (SEQ. ID. NO: 1), PTSPSYSPTSPSYS (SEQ. ID. NO: 2), TKDPSRVG (SEQ. ID. NO: 3), and TQDPSRVG (SEQ. ID. NO: 4). The invention is also directed to an isolated polypeptide comprising an amino acid sequence of from 4 to about 30 amino acids, wherein the amino acid sequence includes the epitope D-X-S-R (SEQ. ID. NO: 5), wherein X is any natural or unnatural amino acid.

Figure 7:
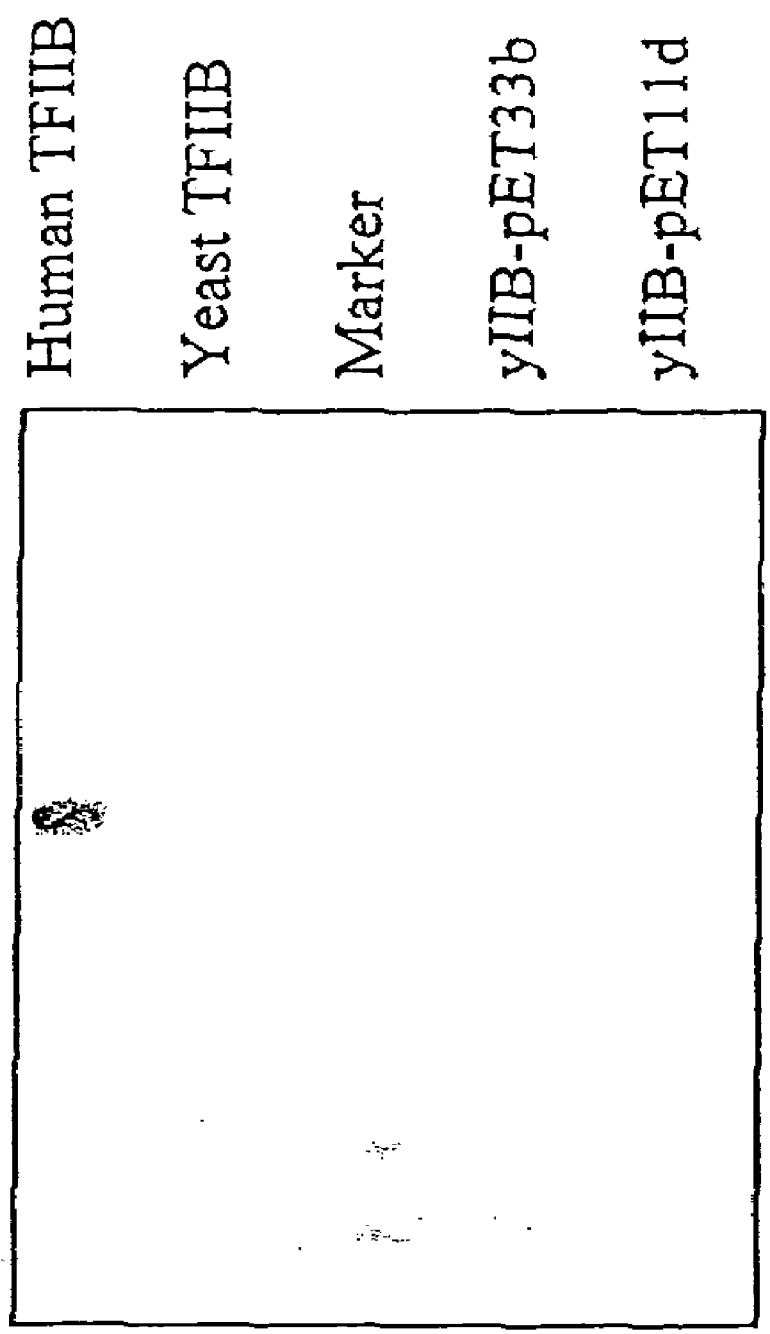

FIG. 7. Western blot showing lack of IIB8 reactivity with yeast TFIIB. mAb IIB8 shows strong affinity to human TFIIB, but does not react with purified yeast TFIIB or yeast TFIIB induced in two vector systems.

Figure 8:
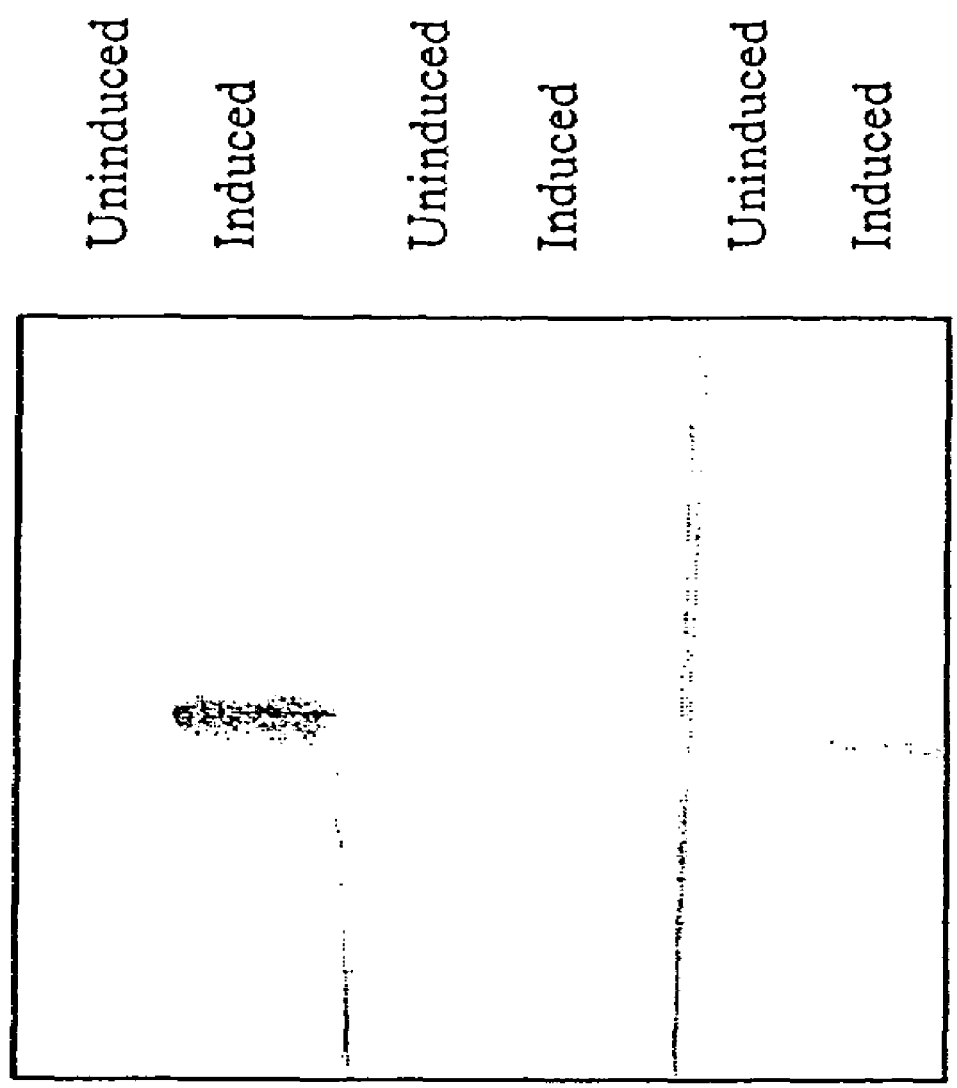
Figure 9:
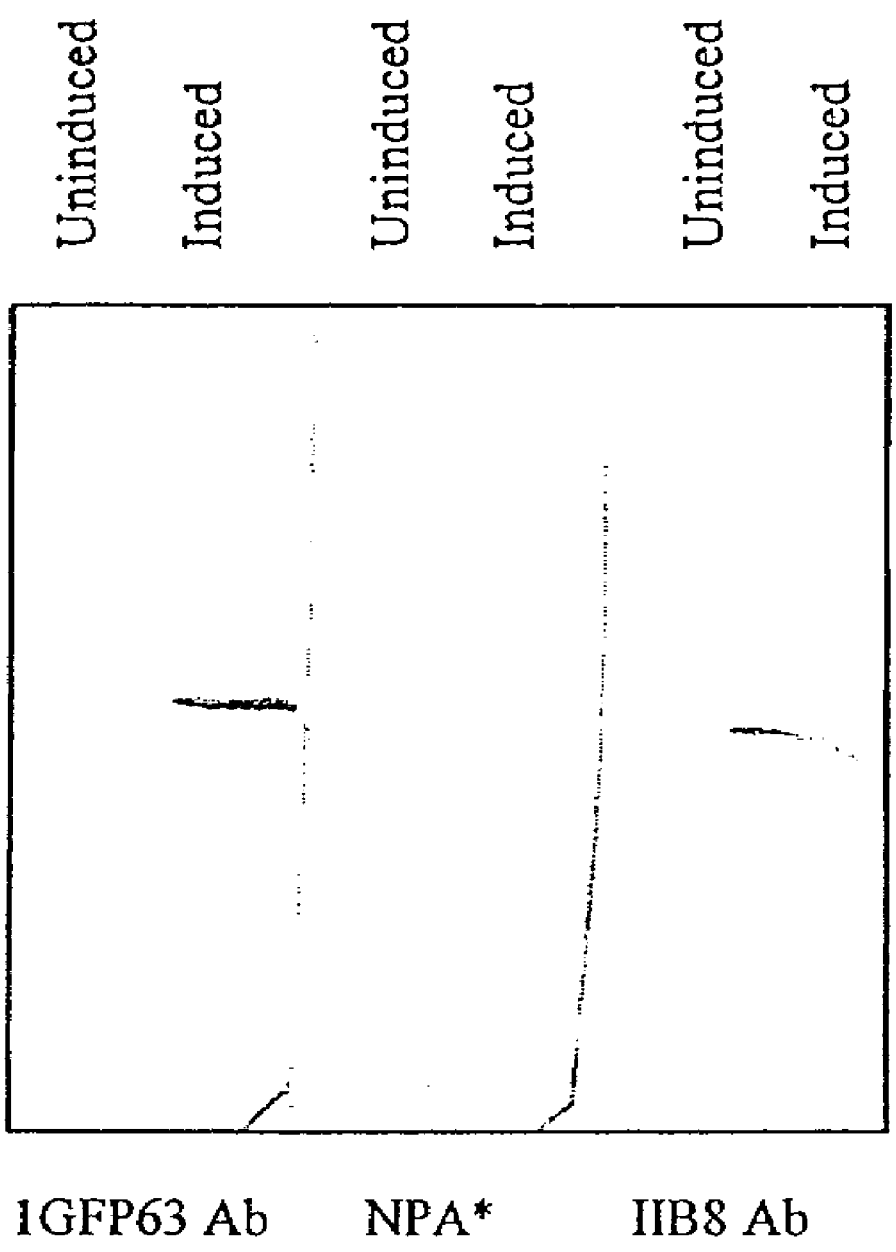

FIGS. 8 and 9. Western blot on fusion proteins containing yIIB epitope variations. FIG. 8 shows GFP-yIIB fusion protein uninduced and induced whole cell extract probed with both mAbs 1GFP63 and IIB8. FIG. 9 mAbs 1GFP63 and IIB8 used as probes for the GFP-hIIBK2D fusion protein. mAb IIB8 shows weak affinity for both epitope tags. *NPA: No primary antibody used.

Figure 10A:
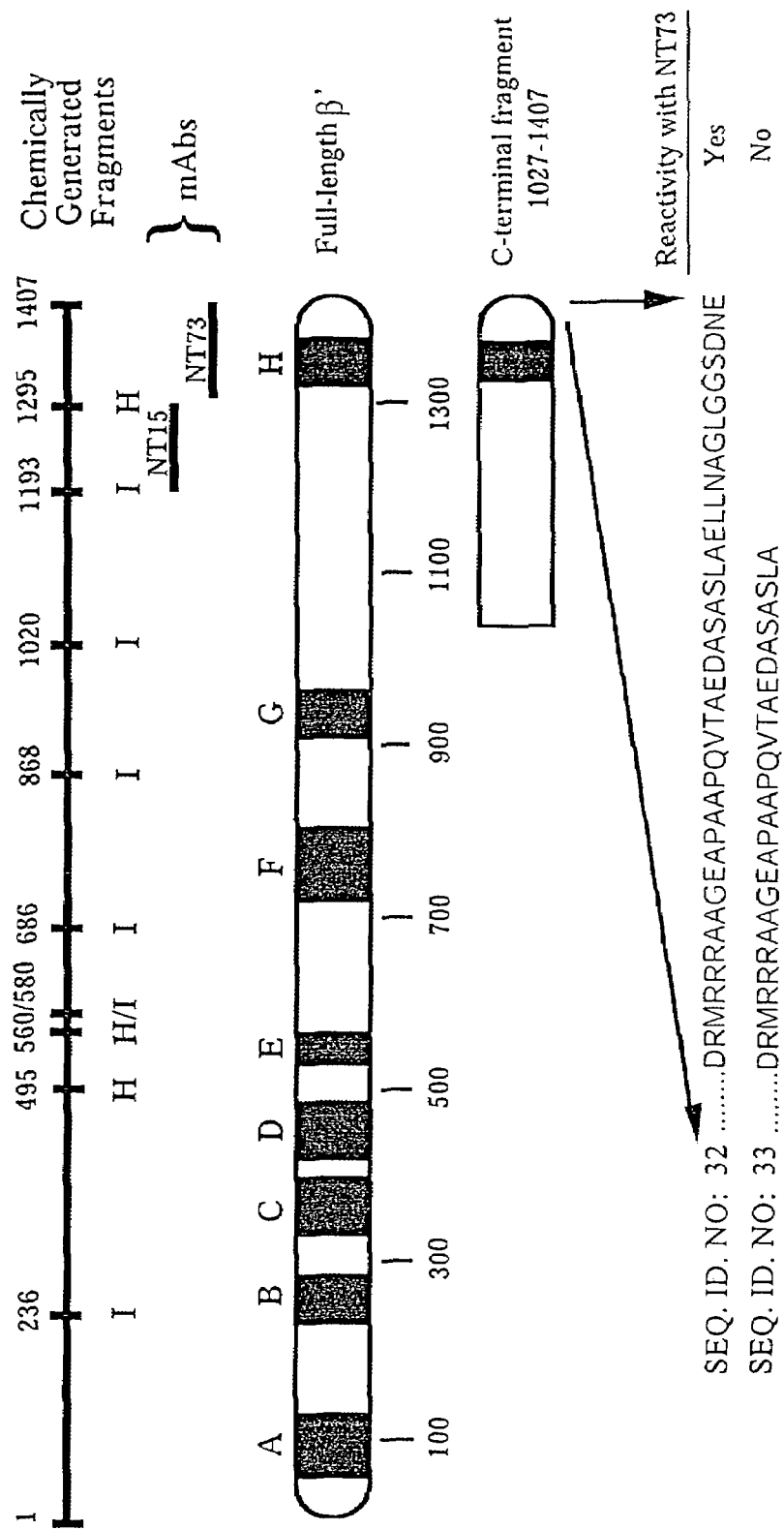
Figure 10B:
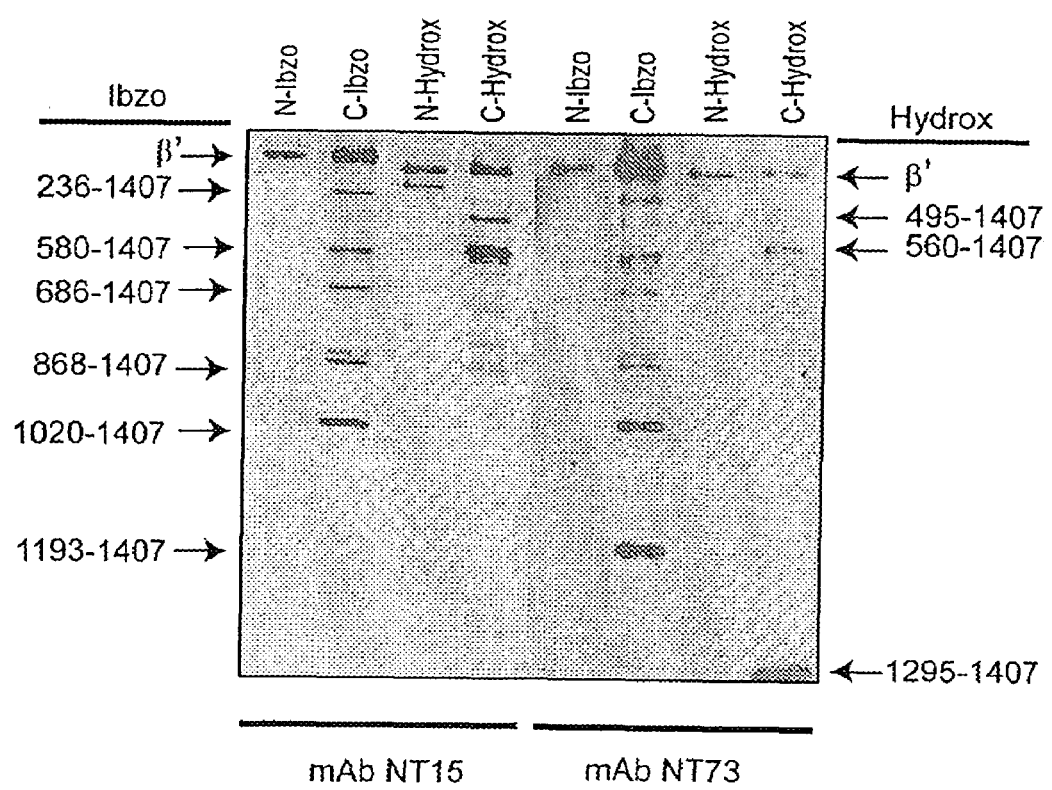
Figure 10C:
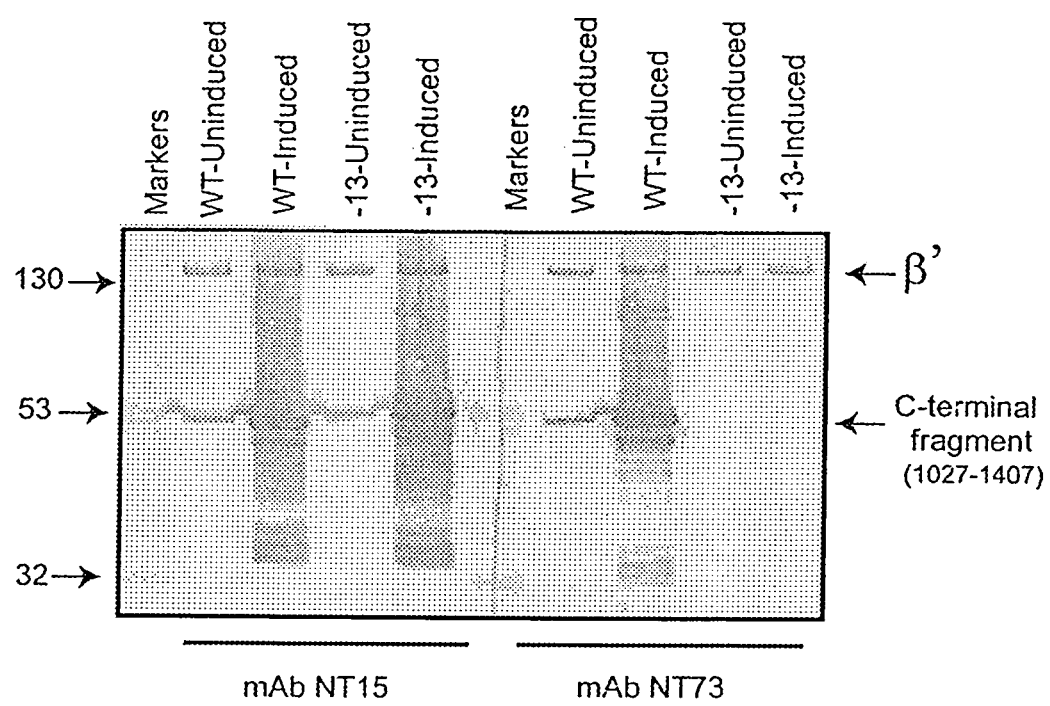

FIGS. 10A, 10B, and 10C. "Ordered-fragment ladder" and deletion mapping of the NT73 epitope to the C-terminus of the β' subunit. FIG. 10A is a schematic representation of the β' subunit showing the sites of chemical cleavage by hydroxylamine (H) and iodosobenzoic acid (I) that could be reliably identified. The regions containing the epitopes for mAbs NT15 and NT73 are indicated, as is the C-terminal fragment that was used to generate the deletions. FIG. 10B is a Western blot prepared from a 8–16% Tris-glycine gel showing the reactivity of NT15 and NT73 with the ordered fragment ladder generated by hydroxylamine (Hydrox) or iodosobenzoic (Ibzo) acid cleavage of either the N- or C-terminally $His_6$-tagged protein. The fragment sizes indicated refer to peptides generated by chemical cleavage of the C-terminally $His_6$-tagged protein. The Ibzo fragments are labeled on the left and the Hydrox fragments are labeled on the right. FIG. 10C is a Western blot prepared from a 12% Tris-glycine gel showing the reactivity of mAbs NT15 and NT73 with the C-terminal fragment (1027–1407) and the fragment containing a deletion of the last 13 amino acids (−13). Whole cell-extracts of uninduced and induced cultures were loaded. The fragment containing the deletion runs larger because the endogenous termination signals were removed by the deletion method.

Figure 11B:
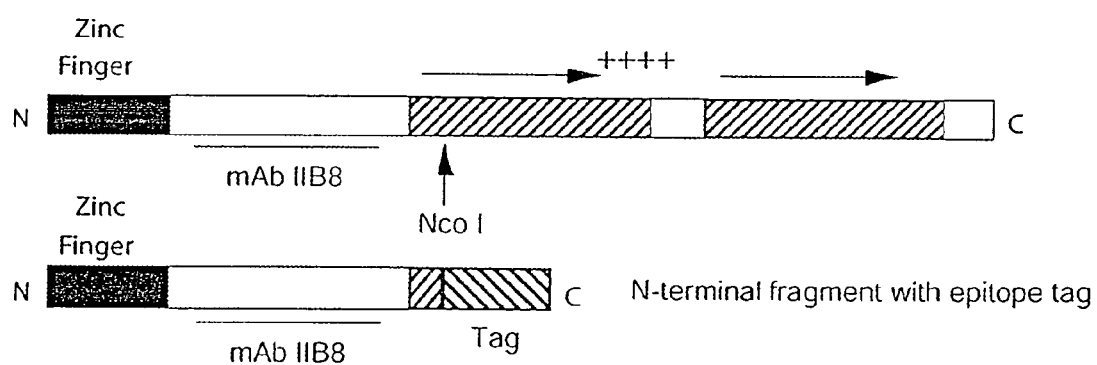
Figure 11C:
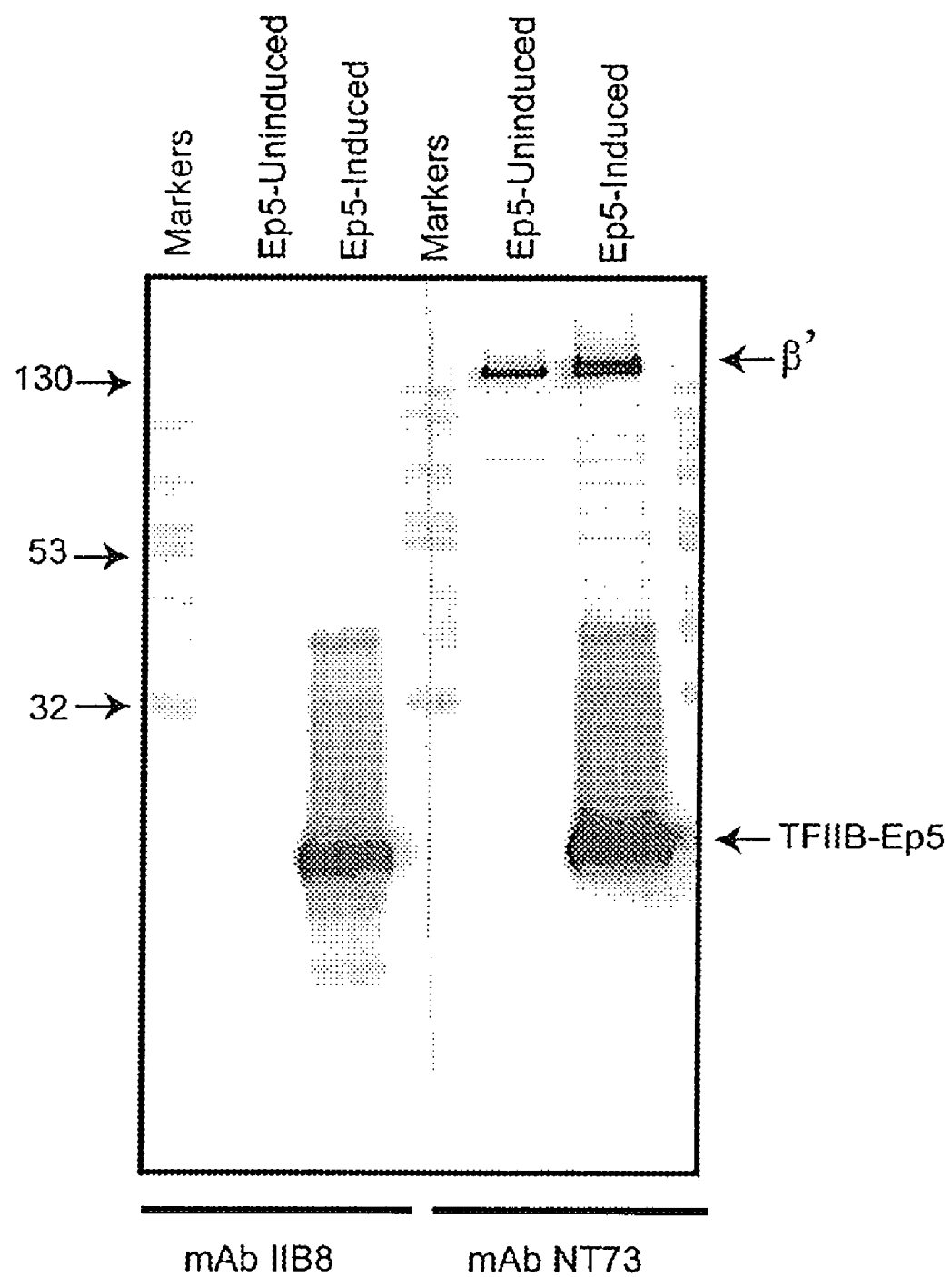

FIGS. 11A, 11B, and 11C. Epitope mapping of the mAb NT73 epitope using peptide tags. FIG. 11A is a schematic representation of the tags generated and their reactivity with mAb NT73. FIG. 11B is a schematic representation of the positioning of the tag on the C-terminus of a fragment of human TFIIB. FIG. 11C is a representative Western blot prepared from a 12% Tris-glycine gel showing the reactivity of mAb NT73 (and the control mAb IIB8) with the ep5 tag on the fragment of TFIIB. Whole cell-extracts of uninduced and induced cultures were loaded.

Figure 12A:
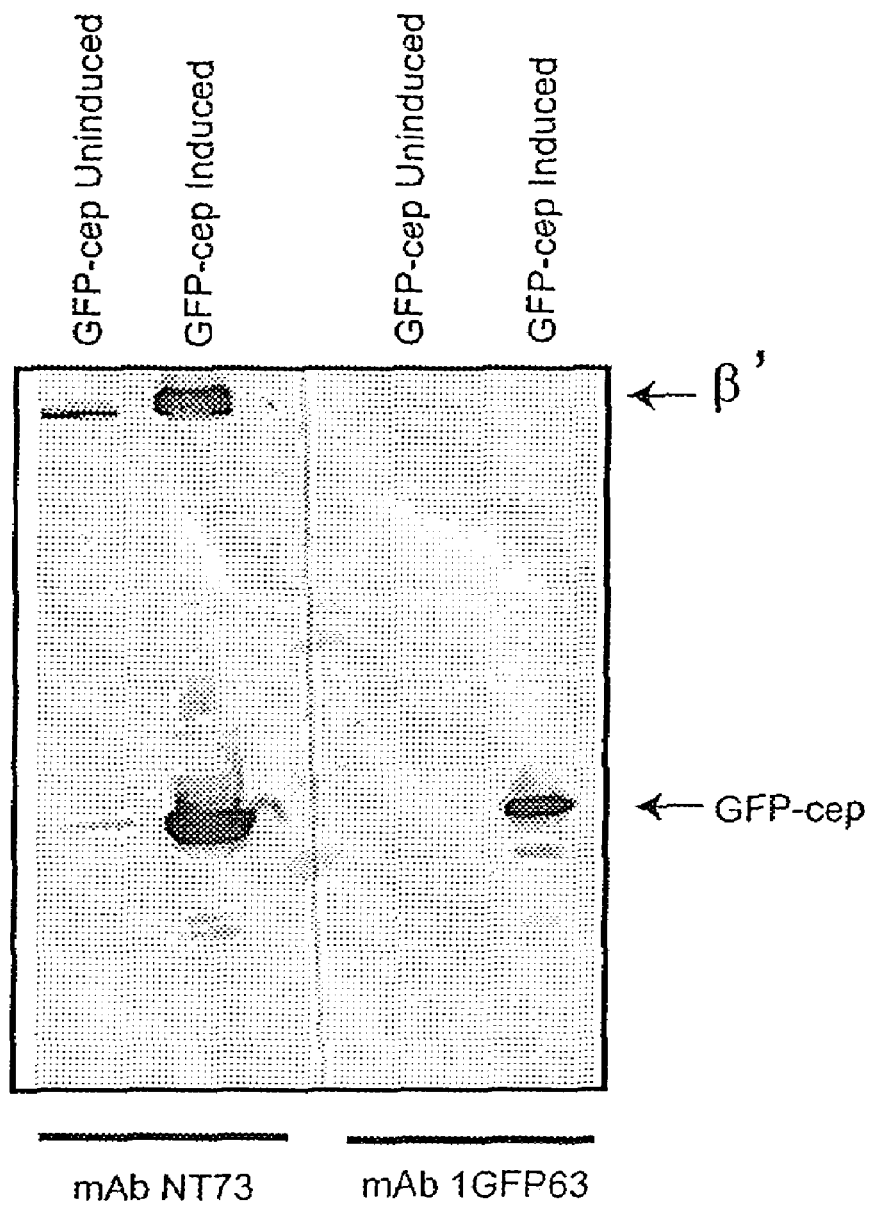
Figure 12B:
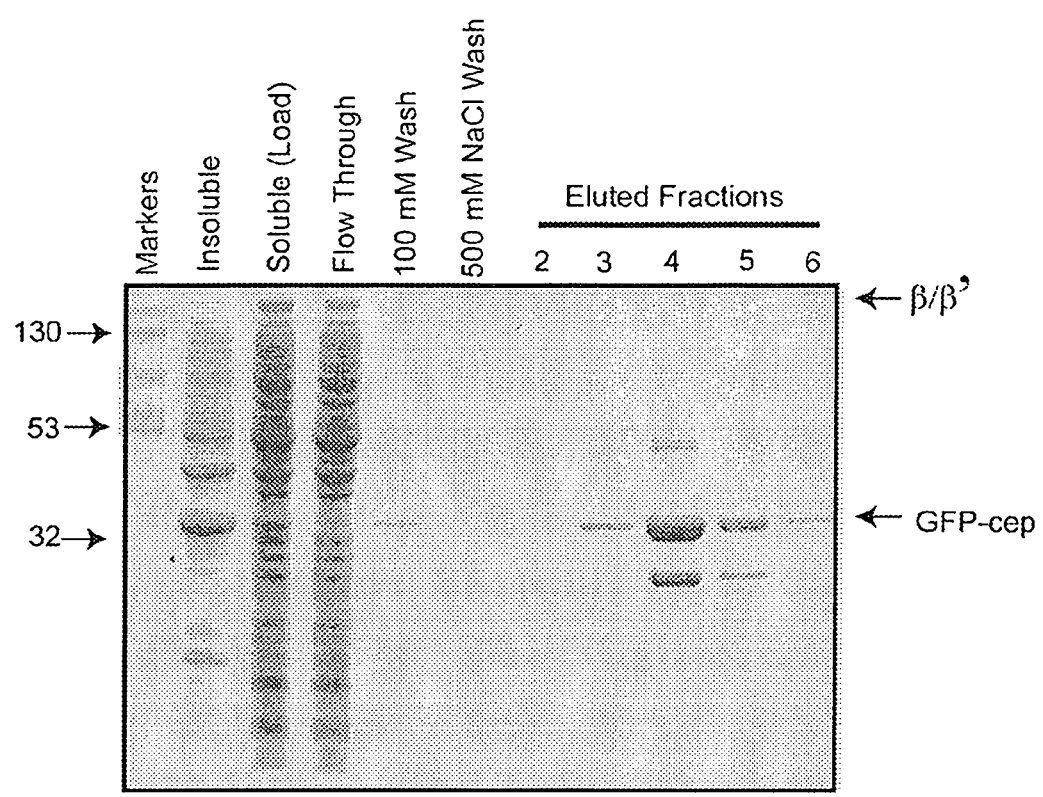
Figure 12C:
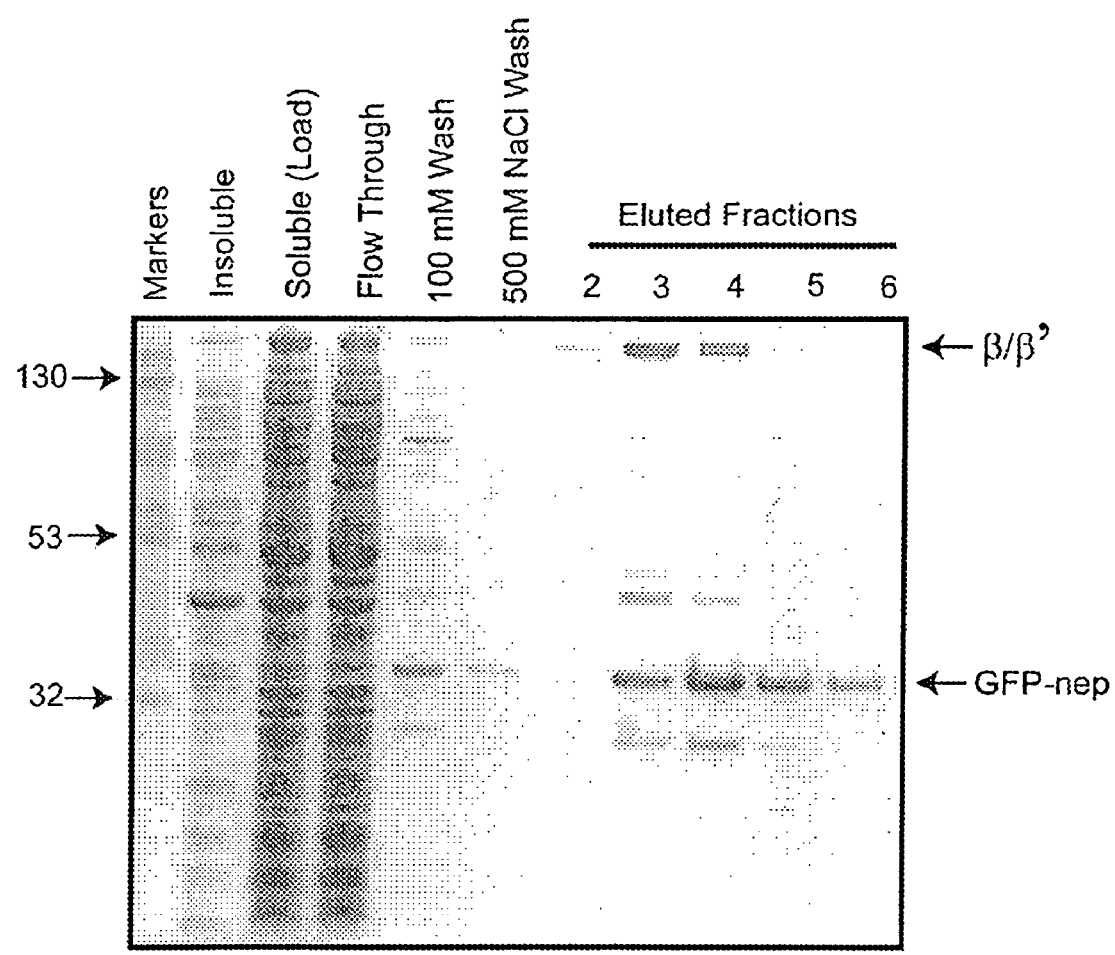
Figure 12D:
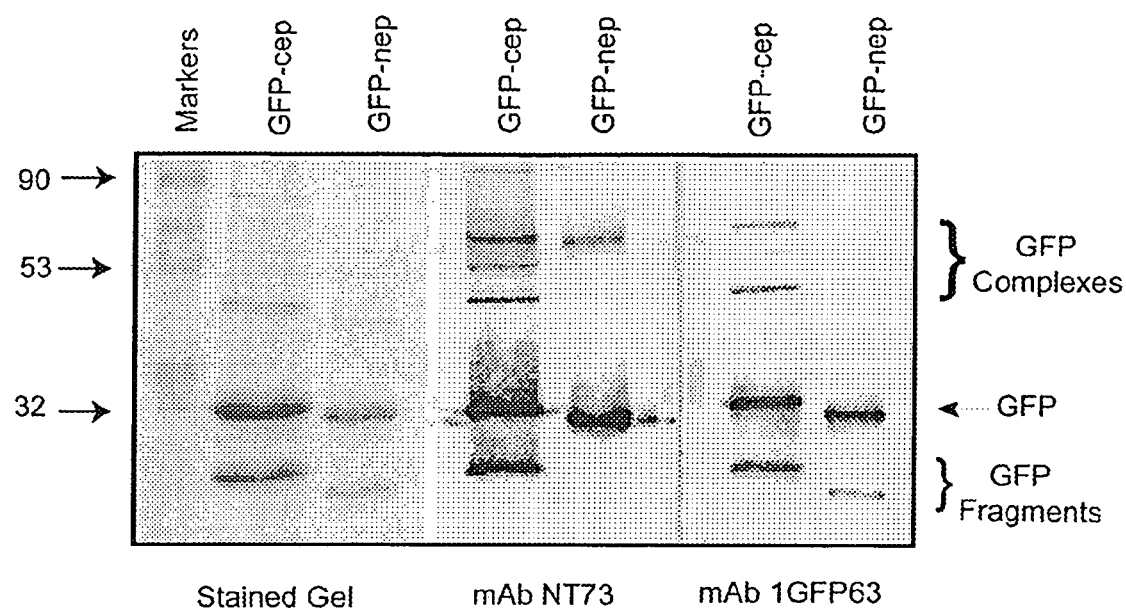

FIGS. 12A, 12B, 12C, and 12D. Purification of epitope-tagged GFP. FIG. 12A is a Western blot prepared from a 12% Tris-glycine gel showing the reactivity of NT73 with the epitope tag on the C-terminus of GFP (GFP-cep). mAb 1GFP63 is a mAb raised against GFP. Whole cell-extracts of the uninduced and induced cultures were loaded. FIG. 12B is an SDS-PAGE gel showing the purification of GFP-cep after purification on NT73-Sepharose. FIG. 12C is an SDS-PAGE showing the purification of the N-terminally epitope tagged-GFP (GFP-nep) after purification on NT73-Sepharose. FIG. 12D is a Western blot prepared from a 15% Tris-glycine gel showing the reactivity of the purified polypeptides with mAb NT73 and mAb 1GFP63.

Figure 13:
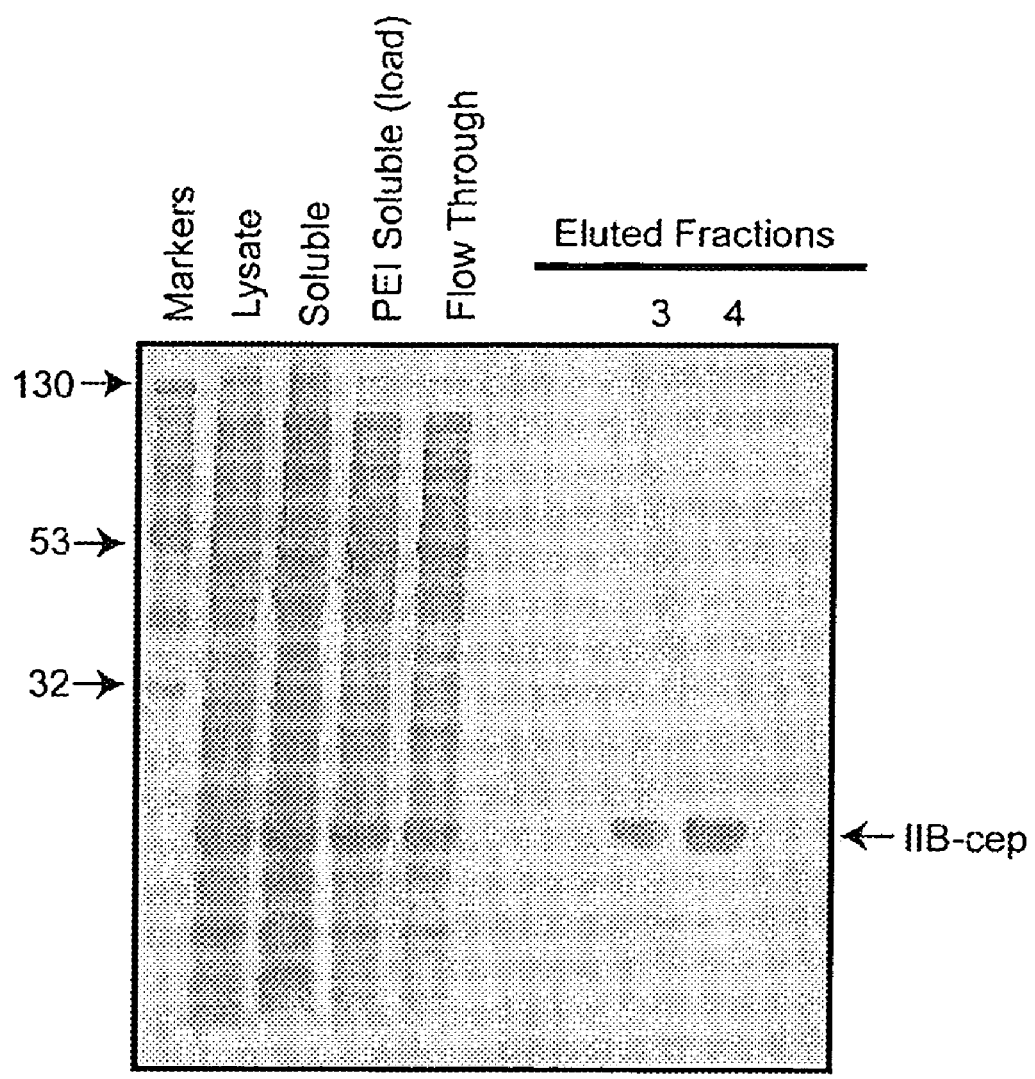

FIG. 13. Purification of epitope-tagged TFIIB fragment. FIG. 13 is an SDS-PAGE gel (12% Tris-glycine gel) of the various steps in the purification of epitope-tagged TFIIB fragment on NT73-Sepharose.

Figure 14A:
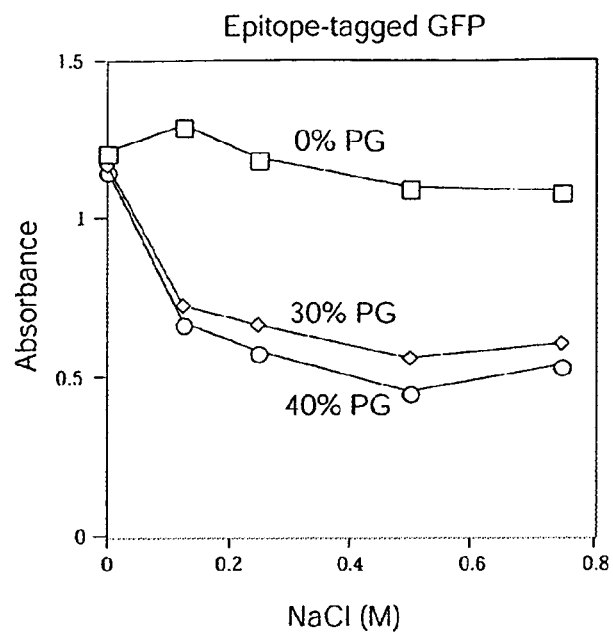
Figure 14B:
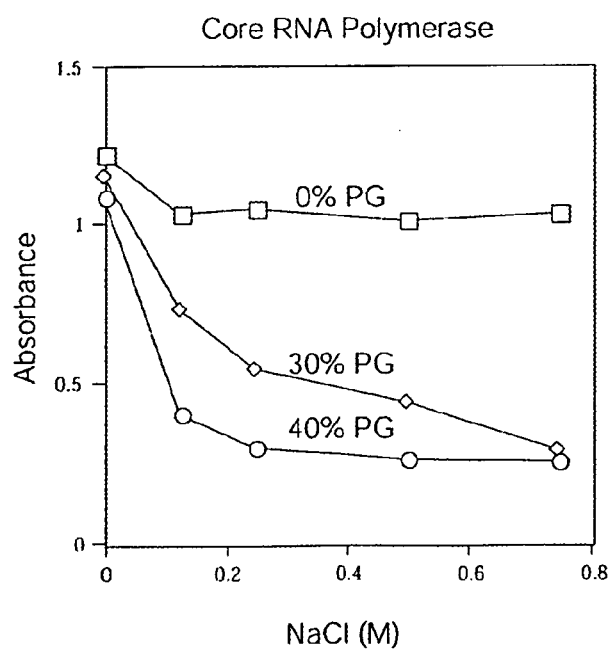

FIGS. 14A and 14B. Polyol-responsiveness of the epitope-tagged GFP. Each point represents the average of duplicate samples. FIG. 14A is a graph depicting the results of an ELISA-elution assay showing the response of mAb NT73 reacted with the C-terminally tagged-GFP to combinations of NaCl and propylene glycol (PG). FIG. 14B is a graph depicting the results of an ELISA-elution of the response of NT73 reacted with core RNA polymerase.

DETAILED DESCRIPTION OF THE INVENTION

Because developing PR-mAbs is a time-consuming procedure, the present invention is directed to epitope tags that are used to enable proteins that lack a corresponding PR-mAb to be purified by the PR-mAb immunoaffinity chromatographic procedure.

An epitope tag (designated "Softag 1" and described in Appendix A, attached hereto and incorporated herein) was recently designed for a highly useful PR-mAb, termed NT73 [13]. The amino acid sequence of Softag 1 is SLAELLNGLGGS (SEQ. ID. NO: 1). This PR-mAb reacts with the β' subunit of *Escherichia coli* RNAP. The epitope-tagged *E. coli* RNAP fusion protein was expressed in *E. coli* and successfully purified from the soluble protein fraction by a single-step immunoaffinity chromatography procedure using the NT73 PR-mAb. Because there is also endogenous, un-tagged RNAP present that reacts with mAb NT73 in *E. coli*, a small amount of unmodified RNAP was also purified with the fusion protein. A second epitope tag (designated "Softag 2") has the amino acid sequence PTSPSYSPTSPSYS (SEQ. ID. NO: 2).

PR-mAb IIB8 recognizes an epitope near the N-terminus of human transcription factor IIB (TFIIB). The epitope of this mAb [11] has been identified and used as a purification tag in *E. coli*. PR-mAb IIB8 does not cross-react with any endogenous prokaryotic proteins, and thus allows separation of the fusion protein from *E. Coli* crude extract. A version of this epitope tag (designated "Softag 3") provides another approach to purifying proteins rapidly, under non-denaturing conditions.

Thus, the invention is directed to a method of isolating, purifying, or concentrating a target compound. The method comprises first conjugating the target compound to an epitope for a polyol-responsive monoclonal antibody (PR-mAb) to yield a conjugate. The resulting conjugate is then contacted to an immunoaffinity matrix comprising a PR-mAb specifically reactive with the epitope, whereby the conjugate is selectively adsorbed to the matrix. The matrix is then rinsed with a buffer to remove any non-specifically adsorbed non-target material. The matrix is then eluted with a buffer comprising a polyol and a non-chaotropic salt, whereby the adsorbed target compound is eluted from the matrix.

The target compound can be conjugated directly to the epitope or the target compound can be conjugated to the epitope via a linker. If a linker is present, it is preferred that the linker is thermolabile, chemically labile, or a recognition/cleavage site for an enzyme. This allows the epitope to be disassociated from the target compound via heat, using appropriate chemicals, or by digestion using a suitable enzyme (respectively). In the preferred embodiment, the linker is a polypeptide that defines the recognition/cleavage site for a peptidase or protease.

A host of suitable recognition/cleavage sequences are known in the art. For example, the following enzymes and their corresponding amino acid recognition/cleavage sequences are known (vertical line designates the cleavage point):

TABLE 1

Recognition Sequences

| Protease | Recognition Sequence | | Commercial Source |
|---|---|---|---|
| Factor Xa | Ile Glu/Asp Gly Arg \| | (SEQ. ID. NO: 6) | New England Biolabs |
| Enterokinase | Asp Asp Asp Asp Lys \| | (SEQ. ID. NO: 7) | New England Biolabs |
| Thrombin | Leu Val Pro Arg \| Gly Ser | (SEQ. ID. NO: 8) | New England Biolabs |
| TEV protease | Glu Asn Leu Tyr Phe Gln \| Gly | (SEQ. ID. NO: 9) | Life Technologies |
| PreScission | Leu Glu Val Leu Phe Gln \| Gly Pro | (SEQ. ID. NO: 10) | Amersham/Pharmacia |

TABLE 2

Restriction Endonucleases

| Restriction Enzyme | Source | DNA Sequence Recognized | Ends of Cleaved Molecule |
|---|---|---|---|
| EcoRI | *Escherichia coli* | 5'-GAATTC<br>3'-CTTAAG<br>(SEQ. ID. NO: 11) | 5'AATTC -- G<br>G -- CTTAA5' |
| BamHI | *Bacillus amyloliquefaciens* | 5'-GGATCC<br>3'-CCTAGG<br>(SEQ. ID. NO: 12) | 5'GATCC -- G<br>G -- CCTAC5' |
| HindIII | *Haemophilus influenzae* | 5'-AAGCTT<br>3'-TTCGAA<br>(SEQ. ID. NO: 13) | 5'AGCTT -- A<br>A -- TTCGA5' |
| MstII | *Microcoleus* species | 5'-CCTNAGG<br>3'GGANTCC<br>(SEQ. ID. NO: 14) | 5'CTNAGG--C<br>C--GGANTC5' |
| TaqI | *Thermus aquaticus* | 5'-TCGA<br>3'-AGCT<br>(SEQ. ID. NO: 15) | 5'CGA - T<br>T - AGC5' |
| NotI | *Nocardia otitidis* | 5'-GCGGCCGC<br>3'CGCCGGCG<br>(SEQ. ID. NO: 16) | 5'CGCCGC-GC<br>CG-CGCCGG5' |
| AluI* | *Arthrobacter luteus* | 5'-AGCT<br>3'-TCGA<br>(SEQ. ID. NO: 17) | 5'AG -- -- -- CT<br>TC -- -- -- GA5' |

*= blunt ends

Alternatively, the linker (when one is present) can comprise a recognition/cleavage site for a restriction endonuclease. A host of suitable sequences are known in the art. See Table 2 (above) for a non-limiting list of exemplary sequences.

In a particularly preferred embodiment, the invention is drawn to a method of isolating, purifying, or concentrating a target polypeptide or protein. Here, the method comprises providing a fusion protein comprising the target polypeptide or protein and an epitope for a PR-mAb. The fusion protein is then contacted to an immunoaffinity matrix comprising a PR-mAb specifically reactive with the epitope. As noted above, the fusion protein may optionally further comprise a linker disposed between the target polypeptide or protein and the epitope.

In another embodiment, the invention links or otherwise operationally connects an epitope for a PR-mAb to a probe compound, rather than to the target compound. Here, the method conjugates a probe compound capable of binding to the target compound to an epitope for a PR-mAb to yield a conjugate. The epitope/probe conjugate is then admixed or contacted to a sample suspected of containing the target compound. This is done under conditions and for a time sufficient to allow the test compound to bind to the probe portion of the probe/epitope conjugate. This yields a probe/target mixture. The probe/target mixture of step (b) is then contacted to an immunoaffinity matrix comprising a PR-mAb specifically reactive with the epitope. This causes the probe/target complexes within the probe/target mixture to adsorb to the immunoaffinity matrix. The complexes can then be eluted from the matrix using the polyol solutions described herein.

The invention is also directed to a composition of matter comprising a target compound conjugated to an isolated polypeptide having an amino acid sequence selected from the group consisting of: SLAELLNGLGGS (SEQ. ID. NO: 1), PTSPSYSPTSPSYS (SEQ. ID. NO: 2), TKDPSRVG (SEQ. ID. NO: 3), and TQDPSRVG (SEQ. ID. NO: 4), SEQ. ID. NOS: 3 and 4 are preferred.

The invention is further directed to a composition of matter comprising: a target compound, a linker, and an isolated polypeptide, wherein the target compound is conjugated to the linker, and the linker is conjugated to the isolated polypeptide, and further wherein the isolated polypeptide has an amino acid sequence selected from the group consisting of: SLAELLNGLGGS (SEQ. ID. NO: 1), PTSPSYSPTSPSYS (SEQ. ID. NO: 2), TKDPSRVG (SEQ. ID. NO: 3), and TQDPSRVG (SEQ. ID. NO: 4).

A still further embodiment of the invention is an isolated polypeptide having an amino acid sequence selected from the group consisting of: SLAELLNGLGGS (SEQ. ID. NO: 1), PTSPSYSPTSPSYS (SEQ. ID. NO: 2), TKDPSRVG (SEQ. ID. NO: 3), and TQDPSRVG (SEQ. ID. NO: 4). The invention also includes anisolated polypeptide comprising an amino acid sequence of from 4 to about 30 amino acids, wherein the amino acid sequence includes the epitope D-X-S-R (SEQ. ID. NO: 5), wherein X is any natural or unnatural amino acid.

As used herein, the term "immunoaffinity matrix" denotes an inert matrix having immobilized thereto a PR-mAb. The PR-mAbs to be utilized in the present invention can be from any source without limitation, and generated by any means now known or developed in the future, without limitation.

The current best mode to isolate, optimize, and use murine PR-mAbs is presented in Table 3. The PR-mAb screening methodology outlined in Table 3 uses an extension of standard hybridoma isolation techniques to identify useful PR-mAb antibody-producing cell lines. See the references cited in Table 3 for a more detailed set of protocols and methods to generate PR-mAbs.

TABLE 3. Steps to Isolate, Optimize, and Use PR-mAbs:
1. Immunize mice with protein of interest, boost, and isolate spleen cells.
2. Prepare monoclonal antibody-producing immortal cell lines, either by:
    a. Standard hybridoma approach—fuse spleen cells with mouse myeloma cells, and select for hybridoma growth by standard methods [23].
    b. ABL-MYC retrovirus transformation approach—infect cells from immunized spleen with ABL-MYC retrovirus, grow cells as mouse ascites [24].
3. Identify plasmacytomas producing mAb's that bind to protein-coated microtiter dish wells using standard ELISA methods [23].
4. Re-screen positive mAb's in duplicate, with one well washed with Tris-EDTA buffer and the other washed with the same buffer containing 1 M NaCl and 40% propylene glycol. A strong ELISA signal with the buffer wash, that is decreased at least 50% by the polyol/salt wash, indicates a polyol-responsive mAb [3].
5. Optimize elution conditions using ELISA elution [3]. The microtiter plate format facilitates the rapid testing of many salt and polyol concentrations to find conditions required to effectively elute the enzyme from a particular mAb while still retaining enzyme activity.
6. Prepare purified mAb from mouse ascites fluid by standard methods [23].
7. Couple mAb to a chromatography support by one of a number of acceptable methods (we usually used mAb immobilized to CNBr-activated Sepharose at about 2.5 mg/ml of column resin [3]).
8. Apply a protein preparation to the immunoaffinity chromatography resin either in batch or column mode, wash under non-elution conditions, and then elute in <u>column</u> mode with the optimal polyol/salt mixture [3].

Polyol-responsiveness is not a property of only one antibody or antigen. A partial list of antigens to which PR-mAbs have been prepared is given in Table 4. There does not appear to be any correlation between the isotype of any given mAb and whether the mAb is polyol-responsive. As a general rule of thumb, between about 5% and about 10% of ELISA-positive hybridomas (murine or rat-derived) produce PR-mAbs. Although there is variation in binding properties among PR-mAbs, the most thoroughly studied of the PR-mAbs to date (8WG16 and NT73, see Table 4) show similar release properties. In general, elution is more effective at about 20° C. to about 25° C. than at 5° C. While many salts function to drive dissociation of the mAb-antigen complex, NaCl and ammonium sulfate generally work better that others (such as sodium acetate or potassium glutamate) in that these salts yield clean, reproducible results. (Note that sodium acetate, potassium glutamate, as well as other salts, can be used to drive dissociation; NaCl and ammonium sulfate, however, are preferred.) Several different low molecular-weight polyols also function to dissociate the PR-mAb-antigen complex, generally in the order of: propylene glycol or 2,3-butanediol>ethylene glycol>>glycerol (which are the preferred polyols for use in the invention). A typical elution buffer contains Tris-HCl, pH 7.9, 0.7 M NaCl or 0.75 M ammonium sulfate, 30–40% propylene glycol, and 0.5 mM EDTA. Reducing agents are usually avoided in the elution buffer to prolong the life of the immunoaffinity column. However, reducing agents can be added back immediately to the eluted fractions where necessary or desired.

TABLE 4

Proteins Purified Using Polyol-Responsive MAbs:

| Protein | MAb | References |
| --- | --- | --- |
| E. coli RNA polymerase β' subunit | NT73 | [3, 25] |
| E. coli RNA polymerase α subunit | 4RA2 | [25] |
| E. coli RNA polymerase sigma70 | 3RD3 | [26] |
| E. coli RNA polymerase β subunit | 8RD13 | [27] |
| Eukaryotic RNA polymerase II Rpb1-CTD | 8WG16 | [25] |
| Transcription factor TFIIB | IIB8 | [25] |
| Transcription factor TBP | 1TBP22 | [29] |
| Transcription factor TFIIF subunit RAP 30 | 1RAP1 | [25] |
| Toluene dioxygenase β subunit | 301β | [9] |
| Histone methylation complex, Set1 | anti-Set1p | [10] |
| Human DNA polymerase δ | anti-pol δ | [8] |
| Mouse and human Apaf1 |  | [Burgess, unpublished] |

PR-mAbs allow proteins to be purified using a gentle immunoaffinity chromatography procedure. These antibodies maintain high affinity interactions, but release the antigen under nondenaturing conditions.

As described herein, the epitope for PR-mAb IIB8 has been identified and can be used as a purification tag. This development allows expansion of the nondenaturing elution method to other systems. In short, the invention is a general method of using defined polyol-responsive epitopes to isolate desired compounds, including polypeptides and proteins. The specific epitope for PR-mAb IIB8 tag is especially useful in isolating, purifying and/or concentrating polypeptides and proteins expressed in prokaryotic cells because no endogenous prokaryotic protein includes the IIB8 epitope. Also, because the endogenous yeast TFIIB epitope is not recognized by IIB8, these tags can also be used to purify desired protein expressed in yeast.

Comparison of an immunoaffinity purification column utilizing PR-mAb NT73 with a Ni-NTA column for purification of E. coli RNAP indicated that purer RNAP was recovered through the immunoaffinity procedure [16]. Preceding the polyol/salt elution with either a high salt alone or polyol alone wash allows reduction of nonspecific binding. Although the cost and time needed for mAb production and affinity resin construction are drawbacks, the mAbs can be expressed as single-chain variable fragments (scFv) in bacteria.

As described in the Examples, the two residues on either side of the consensus sequence were included in the epitope tag to add stability and to allow accessibility for interaction with IIB8 once the tag is fused to the protein of interest. Including one or more flanking residues is not required for the invention to function, but it is preferred. The resulting amino acid composition of the human IIB8 epitope contains three charged residues. Two of these residues are found in the four amino acid consensus sequence indicated by phage display. The other charged amino acid, located at position two, was shown to be unnecessary for IIB8 reactivity with the tag; however, replacing the charged residue with a polar amino acid resulted in a more polyol-responsive tag (designated "hIIBK2Q").

The homologous IIB8 epitope region in yeast contains two differences in amino acid sequence. Both of these variations are found outside the consensus sequence. One difference is a change from lysine to aspartic acid at the second position. An epitope tag displaying this variation (designated "hIIBK2D") had considerably lower affinity to IIB8, thus confirming that the amino acid at position two influences IIB8 affinity. The endogenous yeast epitope also contains an inserted glycine between position one and two. This inserted residue may contribute to lower IIB8 affinity, but the reactivity cannot be quantified on a Western blot. Any contribution of the additional amino acid would suggest that the spacing of the polar threonine residue at position one and the rest of the epitope is important (see Table 5 in the Examples).

While hIIBK2D and yIIB are not preferred as purification tags (due to their low IIB8 affinity), hIIB and hIIBK2Q are highly efficient when used as purification tags. The GFP fusion protein described in the Examples can be separated out of crude extract by an IIB8-Sepharose immunoaffinity column. The resulting protein is functional as detected by the fluorescence immediately after elution. Though it appears that other proteins co-purify with the fusion protein, the resulting fractions are relatively pure (and vastly purified as compared to crude protein mixture). The additional GFP-related bands are the result of the tendency of GFP to form dimers and degradation products [17].

Figure 3A:
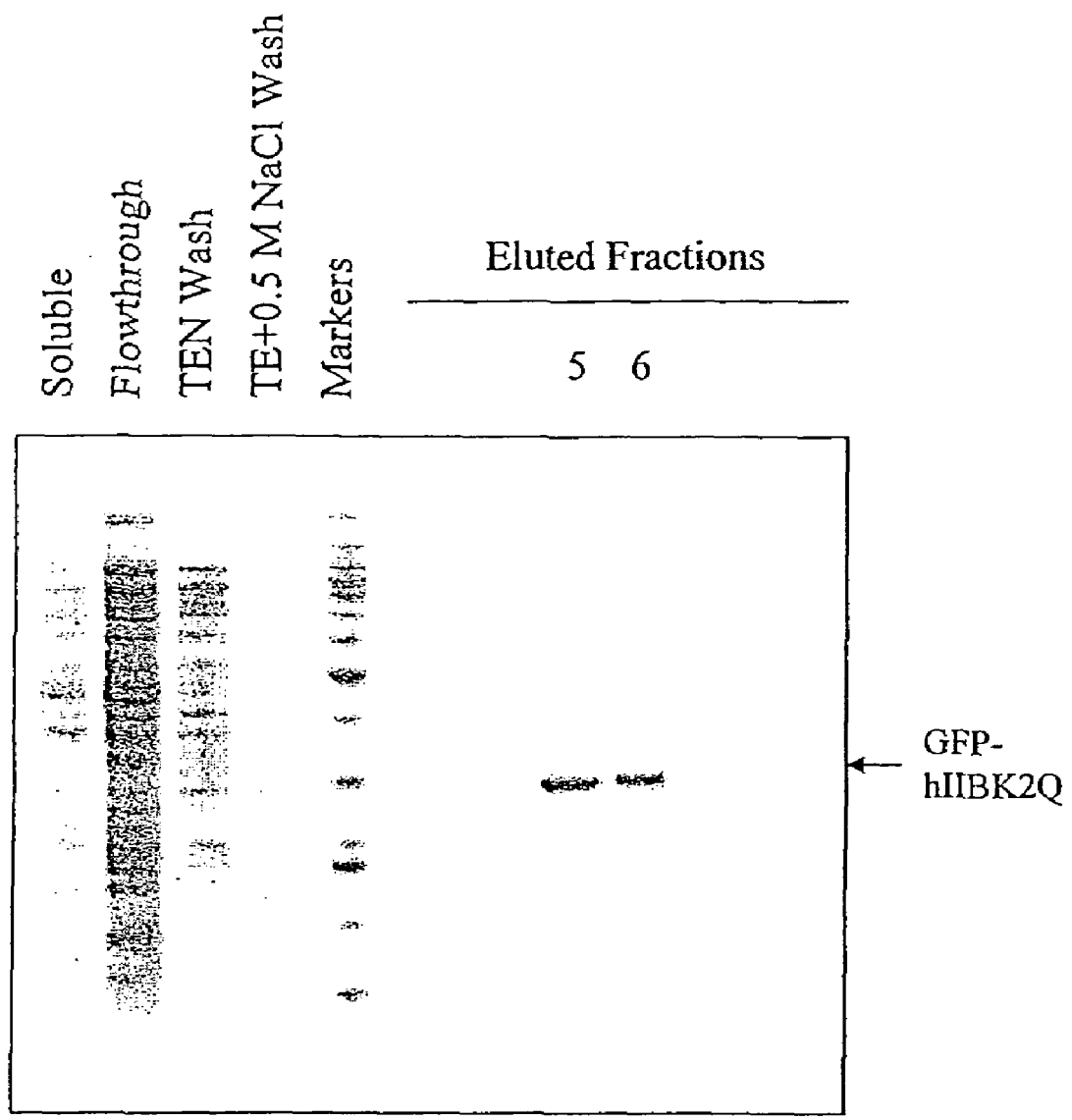
FIG. 3. Purification of epitope-tagged GFP. (A) SDS-PAGE shows purification of GFP-hIIBK2Q on IIB8-Sepharose column. (B) SDS-PAGE shows purification of GFP-hIIB on IIB8-Sepharose column. This column includes an additional wash with TE+40% propylene glycol.
Figure 3B:
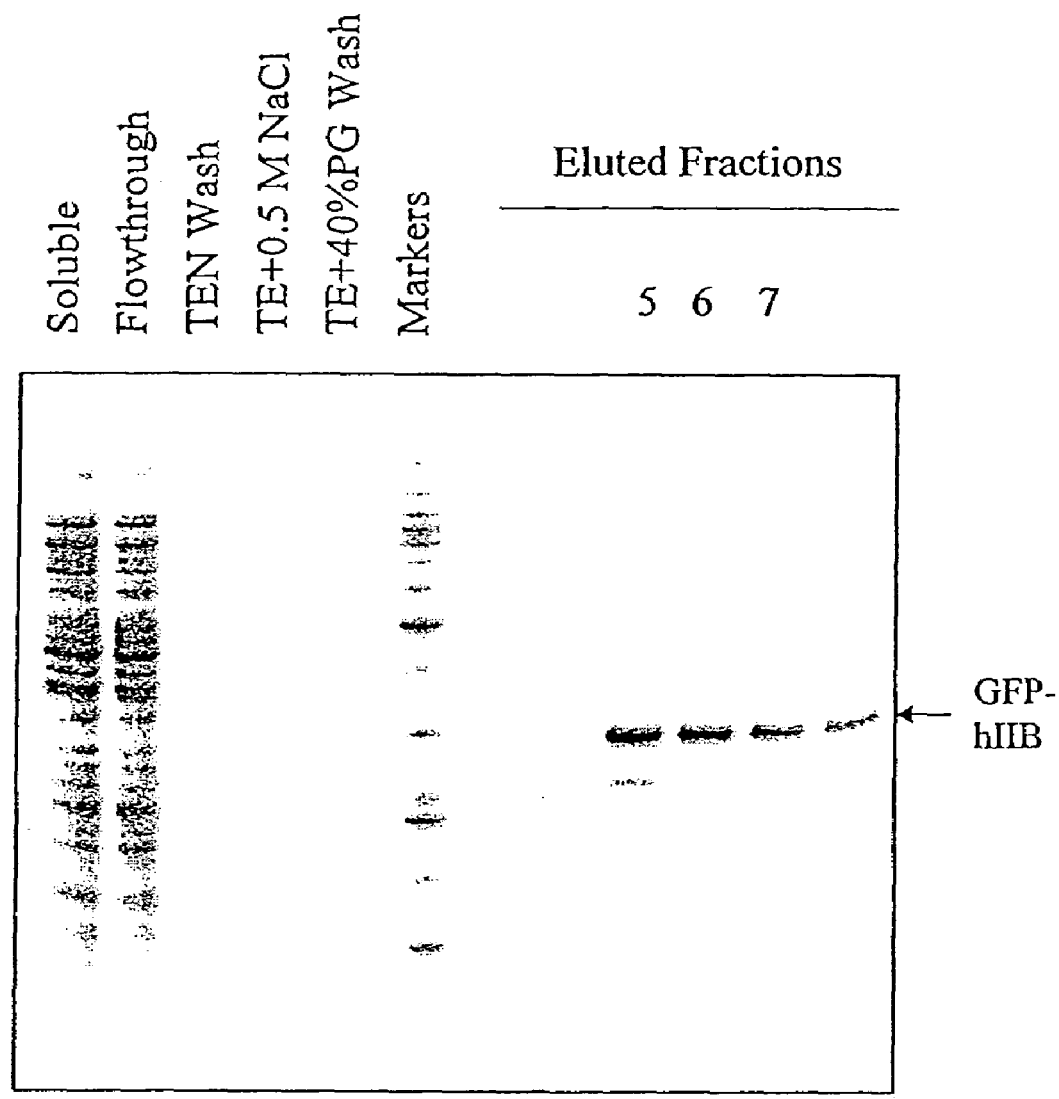

The hIIBK2Q epitope tag eluted more efficiently as seen when comparing the fractions off the immunoaffinity columns (see FIG. 3). The elution for hIIBK2Q was sharper and eluted immediately upon the addition of the elution buffer. The hIIBK2Q epitope tag was also more responsive to the elution buffer in the ELISA-elution assay. This epitope tag showed elution properties more closely associated with the endogenous protein as compared to the hIIB-tagged protein (see FIG. 6). Because hIIBK2Q is a more efficient epitope tag when compared to the other tags, hIIBK2Q has been designated Softag 3.

The difference in polyol-responsiveness between hIIB and hIIBK2Q seen in both the affinity column and the ELISA-elution assays could be associated with the loss of a charged amino acid in the hIIBK2Q tag. While not being limited to any particular underlying biological phenomenon or mechanism, the lysine mutated in hIIBK2Q may be important in providing a strong interaction between antibody and antigen. The charged amino acid in the endogenous protein may be less accessible to IIB8 due to the structure of the protein. However, this residue may be readily accessible on the hIIB epitope tag allowing it to have a stronger interaction with IIB8. The hIIBK2Q epitope tag compensates for the lack of structural hindrance by incorporating an uncharged, polar residue.

Charged amino acids also tend to form salt bridges. The additional charged residue in hIIB may interact with the charged amino acids in the C-terminus of GFP. This interaction could cause the epitope tag to take on an unusual shape resulting in a difference in polyol-responsiveness or affinity to IIB8.

The mechanism of polyol-responsive elution remains unknown. Comparison among the three epitopes identified to date for different PR-mAbs reveals no discernible common characteristics based on charge or hydrophobicity. Hypothetically, the polyol should strengthen hydrophilic interactions, while the nonchaotropic salt strengthens hydrophobic interactions. A luminescent resonance energy transfer (LRET) assay is planned to determine the affinity of the IIB8 antibody for each epitope tag. This experiment will show whether there is a difference in affinity between the two tags or whether it is the elution buffer that affects each tag differently.

Other sequences can also be used as polyol-responsive epitope tags for purification. For example, NusA can also serve as a polyol-responsive epitope tag for purification purposes. NusA is conventionally used in fusion polypeptides to increase the solubility of heterologous proteins expressed in bacteria (i.e., to prevent the recombinant protein from being expressed as an insoluble fusion body). Proteins fused with NusA typically require another sequence tag to facilitate purification. In the present approach, however, a PR-mAb specific to NusA is used isolate NusA fusion proteins without the need for an additional purification tag. The advantage of this embodiment of the invention is that the NusA portion of the fusion protein accomplishes two critical, but entirely distinct, functions: (1) to increase solubility of the fusion protein, while retaining the folding and disulfide bond formation in the desired protein; and (2) to enable the NusA to act as a polyol-responsive antibody epitope, thereby enabling the NusA portion of the fusion protein to function as an immunoaffinity purification tool for the fusion protein.

EXAMPLES

The following Examples are included solely to provide a more complete understanding of the invention disclosed and claimed herein. The Examples do not limit the scope of the invention in any fashion.

Example 1

Reagents and Buffers: All chemicals were obtained from Sigma Chemical Co. (St. Louis, Mo.) unless otherwise specified. All restriction endonucleases were obtained from New England Biolabs (Beverly, Mass.). Ligations were performed with the Rapid DNA Ligation kit from Roche (Indianapolis, Ind.). TE buffer contains 50 mM Tris-HCl, 0.1 mM EDTA, pH 7.9. TEN buffer consists of TE buffer plus 100 mM NaCl. TE+0.5 buffer contains 500 mM NaCl. All pH values were determined at 23° C.

Antibodies: The production, purification, and use of murine $IgG_{2a}$ mAb IIB8 in immunoaffinity chromatography have been described [11]. mAb IIB8 interacts with an epitope located near the N-terminus of TFIIB [12]. mAb 1GFP63 has been described previously [13]. Immunoadsorbents were prepared using purified mAb conjugated to cyanogen bromide-activated Sepharose 4B (Sigma) as previously described [7]. All animal protocols were approved by the University of Wisconsin-Madison Medical School Animal Use and Care Committee.

Oligonucleotides and DNA Amplification and Sequencing: All oligonucleotides for recombinant DNA construction were synthesized by the University of Wisconsin Biotechnology Center (Madison, Wis.). All recombinant DNA constructions were sequenced at the McArdle Laboratory DNA Sequencing Facility (at the University of Wisconsin-Madison) using an ABI PRISM 373 DNA Sequencer (Applied Biosystems, Foster City, Calif.).

Plasmids and Proteins: The plasmid containing the coding region of green fluorescent protein (GFP) in the pET11a vector has been described [13]. Human TFIIB was purified by the immunoaffinity chromatography procedure described previously [11]. $His_6$-tagged TFIIB mutants were purified by Ni-NTA chromatography (Qiagen, Valencia, Calif.). Purified yeast TFIIB was a gift from David Bushnell and Roger Kornberg. Yeast TFIIB in pET11d was from Steve Buratowski.

Protein Expression: Plasmids were transformed into *E. coli* BL21(DE3)pLysS (Novagen, Madison, Wis.). Transformants were cultured in LB broth containing 100 μg ampicillin/ml and 35 μg chloramphenicol/ml. Plasmid yIIB-pET33b was transformed into *E. Coli* BL21(DE3) cells and cultured in LB broth containing 50 μg kanamycin/ml. Cultures were induced at an O.D. (600 nm) of 0.6 with 1 mM isopropylthiogalactoside (IPTG) for 2.5 hours [14]. Cultures expressing the epitope-tagged version of GFP were grown at 37° C. and induced at 26° C. to increase the amount of soluble product [13].

SDS-PAGE and Western Blotting: Proteins were separated by SDS-PAGE using 4–12% Bis/Tris NuPAGE polyacrylamide gels (Invitrogen, Carlsbad, Calif.). Western blots were prepared as described previously [7], using a secondary antibody (goat anti-mouse IgG) that was conjugated to alkaline phosphatase and the 5-bromo-4-chloro-3-indolyl phosphate and nitro-blue tetrazolium (BCIP/NBT) reagent as substrate. Pre-stained molecular weight markers (Multimark, Invitrogen) were included on all gels.

Epitope Mapping of mAb IIB8: A library containing a 12-amino acid random peptide sequence displayed on the pIII protein of bacteriophage M13 was supplied by Brian Kay. Screening was performed by the ELISA-based affinity capture protocol [15], using mAb IIB8 as the target protein. Approximately 1 μg of purified mAb IIB8 contained in PBS was used to coat each well of the 96-well polystyrene plate, which was then blocked with 3% BSA contained in PBS. Three rounds of panning were performed with an amplification step after the first panning. Phage recovered from the third panning were isolated by culturing infected bacteria in soft agar and then amplifying each isolate in broth culture. Specificity for mAb IIB8 was confirmed by ELISA, using horseradish peroxidase-conjugated anti-M13 antibody (Amersham Biosciences, Piscataway, N.J.) and appropriate substrate to detect the bound phage. Eight phage were sequenced using the gene III sequencing primers.

The epitope was further defined by generating point mutations. Amino acids 51 and 61–70 of TFIIB were individually mutated to alanine residues using the Quick-Change procedure and pfu polymerase (Stratagene, La Jolla, Calif.). Each mutation was then expressed in *E. coli* and the TFIIB was purified either by immunoaffinity chromatography [11] or by $Ni^{2+}$-NTA chromatography (Qiagen).

Epitope Tagging of GFP: Peptide tags were constructed by using complementary synthetic oligonucleotides, containing the IIB8 epitope, two translational stop codons at the 3' end, and BamH1 sticky ends. The oligonucleotides were phosphorylated with polynucleotide kinase, mixed in equimolar proportions, and heated to 90° C. for 20 min in a heating block. The heating block was then allowed to return to room temperature. The oligonucleotides were ligated into the BamH1 site at the C-terminus of GFP-pET11a [13]. The fusion resulted in the addition of glycine and serine residues between the GFP coding region and the epitope tag. DNA sequencing confirmed that only one tag was included in each fusion protein. The resulting fusion proteins were GFP-GSTKDPSRVG (SEQ. ID. NO: 18) (designated hIB), GFP-GSTQDPSRVG (SEQ. ID. NO: 19) (designated hIIBK2Q), GFP-GSTDDPSRVG (SEQ. ID. NO: 20) (designated hIIBK2D), and GFP-GSTGDDPSRVG (SEQ. ID. NO: 21) (designated yIIB).

Purification of IIB8-tagged Proteins: Frozen cell pellet (1.5 g wet weight) from 1 liter of induced culture was resuspended in 10 ml of TEN buffer. Cells were lysed by sonication (4 rounds of 30-sec bursts on ice). Cell debris and inclusion bodies were removed by centrifugation (27,000 g for 20 min at 4° C.). The soluble fraction was applied to a 4 ml column of IIB8-Sepharose. The column was washed with 10 ml TEN followed by 10 ml TE+0.5 M NaCl. One column used to purify hIIB was also washed with 5 ml TE after the TE+0.5 M NaCl wash followed by TE+40% propylene glycol. Epitope-tagged GFP was eluted with TE+0.75 M ammonium sulfate+40% propylene glycol.

MonoQ Anion-Exchange Column: Peak fractions from the IIB8 immunoaffinity column (totaling 3 ml) were filtered then diluted 50-fold into water. This dilution was loaded onto a MonoQ HR 5/5 column (Amersham Biosciences). After loading, the column was washed with TE buffer. The proteins were eluted using a 0–0.5 M NaCl salt gradient over a 30-minute period with a flow rate of 1 ml per minute. The column was washed with 1 M NaCl to remove any remaining bound proteins. Fractions (1 ml each) were collected.

The four peaks that resulted after salt-gradient elution were separated by SDS-PAGE using 4–12% NuPAGE polyacrylamide gels. Peaks at fraction 21, 28, and 33 were concentrated 40-fold through a spin concentrator (Millipore, Ultrafree, 10 kDa pore size). The flowthrough was concentrated 160-fold. Fraction 9 was not concentrated.

ELISA-Elution Assays: These assays were performed as previously described [2,6], using 30 ng of protein (TFIIB, GFP-hIIB, or GFP-hIIBK2Q) to coat each well. Briefly, mAb IIB8 was reacted with immobilized antigen. After washing, the wells were treated with elution buffer (TE buffer plus various combinations of propylene glycol and ammonium sulfate) for 20 min. After washing, the remaining primary antibody was detected using an enzyme-conjugated secondary antibody and the appropriate substrate.

Results and Significance of Example 1

Figure 1A:
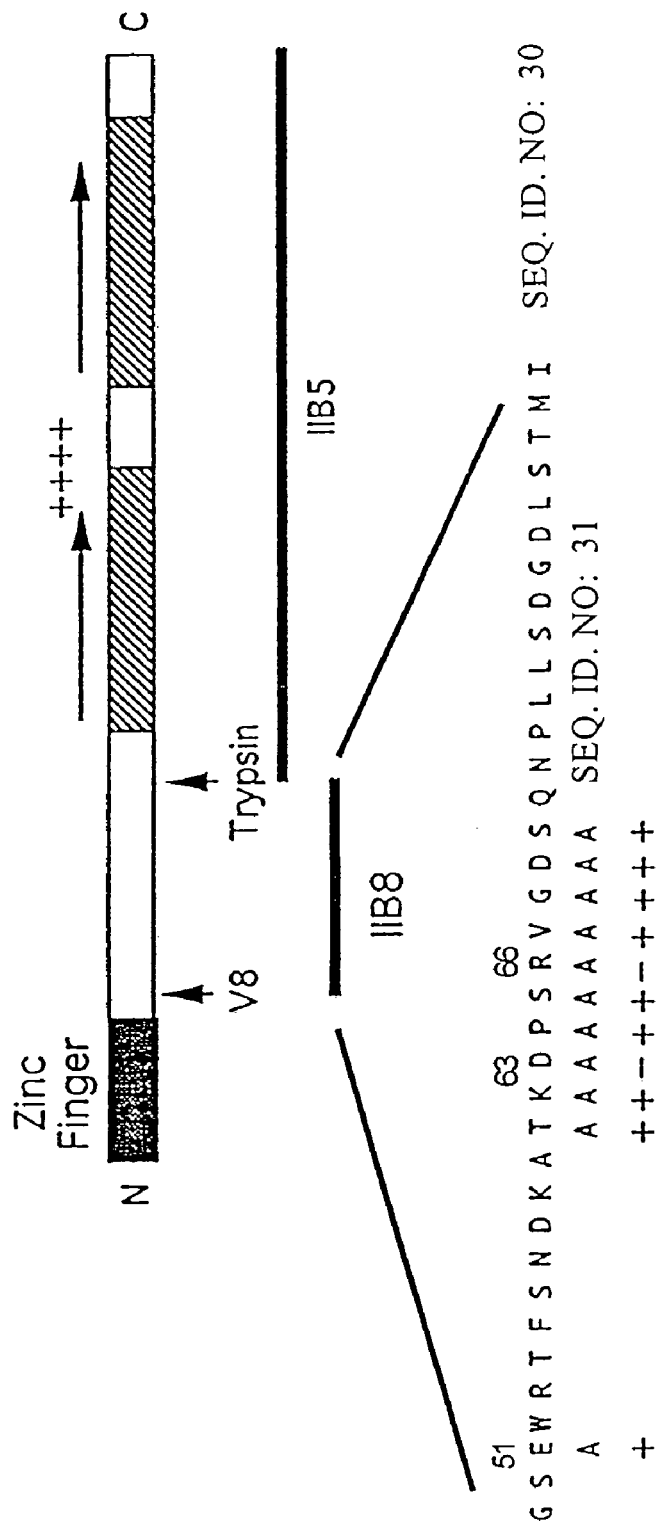
FIG. 1. Epitope mapping of TFIIB. (A) TFIIB protein and previously known regions containing epitopes for IIB8 and IIB5. Selective alanine point mutations are shown. Mutants that bind IIB8 are indicated by "+" while those that lose the ability to bind IIB8 are indicated by "−." (B) The stained gel shows the presence of each protein. *Note: D63A and R66A migrate slower because they are His-tagged. (C) IIB8 antibody cannot recognize mutations at residues 63 or 66 on a Western blot. (D) mAb IIB5 recognizes an epitope in the C-terminus; therefore this probe indicates that all proteins are present.
Figure 1B:
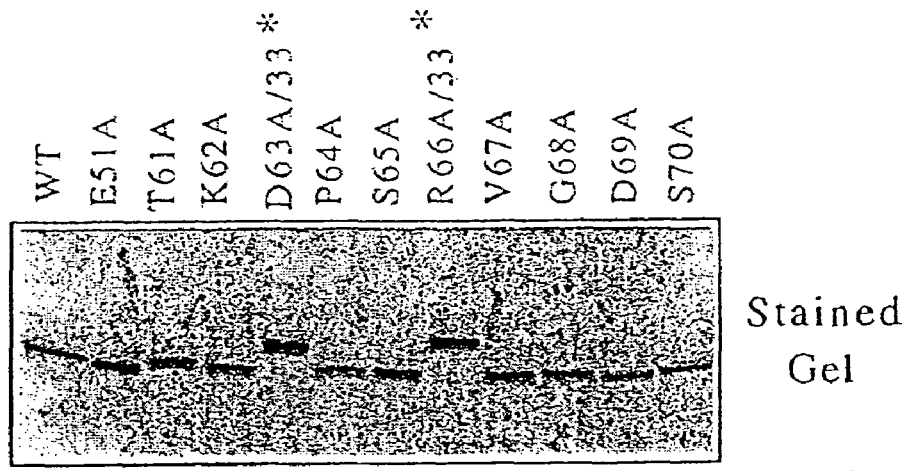
Figure 1C:
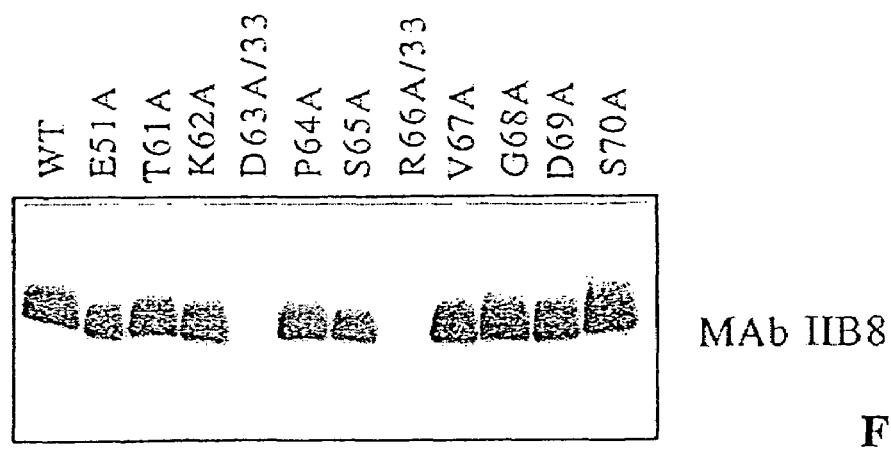
Figure 1D:
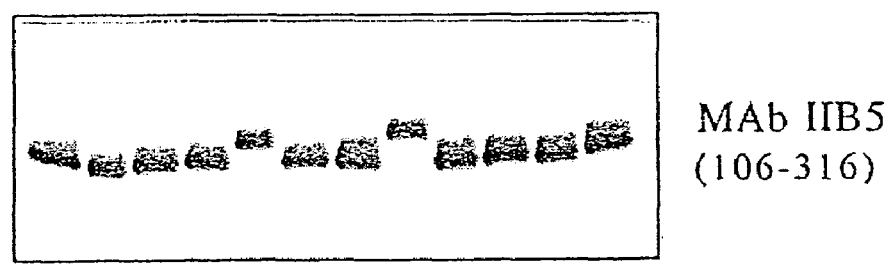

Epitope Mapping: TFIIB plays an essential role in the assembly of the RNA polymerase II initiation complex. The PR-mAb IIB8 inhibits transcription through interaction with this protein near the N-terminus [12]. In order to identify the exact epitope recognized by IIB8, phage display was employed (FIG. 1a). The library consisted of 12-amino acid insertions into the pIII protein of M13 phage. Eight phage were sequenced of which three phage showed the consensus sequence DXSR.

To further test this sequence, selective amino acid mutations were used. Nine (9) residues were individually mutated to alanine in order to see whether this change affected the reactivity of IIB8 to TFIIB on a Western blot (see FIG. 1, panels b–d). Upon mutation of residues 63 and 66, the antibody was no longer reactive. Mutation of residue 65 showed a lower affinity. Based on these results, TKDPSRVG (SEQ. ID. NO: 25) (amino acids 61–68) was hypothesized to be the epitope.

Figure 2A:
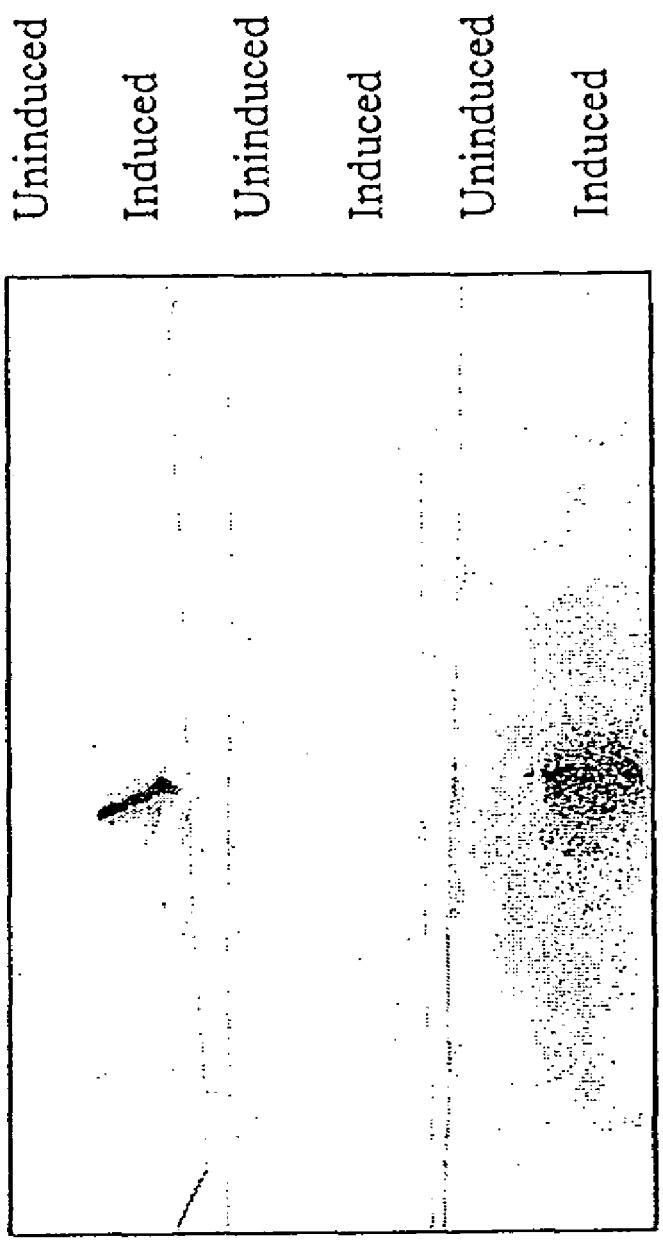
FIG. 2. Generation of fusion proteins. (A) Western blot showing reactivity of IIB8 for GFP-hIIBK2Q. 1 GFP63 is a mAb raised against Green Fluorescent Protein (GFP). Equal amounts of whole cell extract from uninduced and induced cultures were loaded. (B) Western blot showing reactivity of IIB8 and 1GFP63 for hIIB-tagged GFP. Two-fold more whole cell extract was loaded for 1GFP63-probed sample since IIB8 antibody has a higher affinity than 1GFP63. *NPA: No primary antibody used.
Figure 2B:
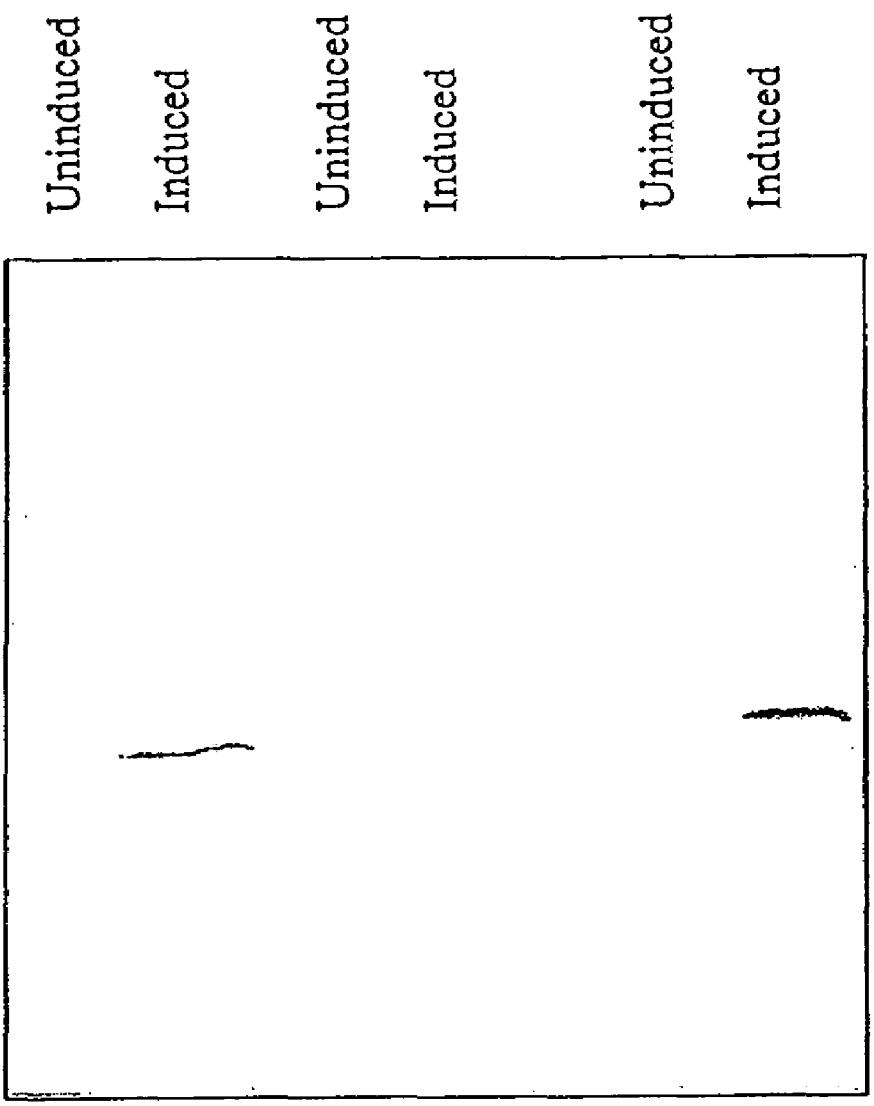

Purification of Epitope-tagged Proteins: To determine whether this epitope is useful in protein purification, it was fused to the C-terminus of GFP. Two fusion proteins resulted due to a point mutation at residue 2 of the epitope. The designation "hIIB" describes the epitope found in the endogenous protein, while the designation "hIIBK2Q" designates the epitope tag containing a point mutation. This mutation causes a change from lysine to glutamine at position two. Western blots showing the expression of these fusion proteins are shown in FIG. 2.

Figure 4:
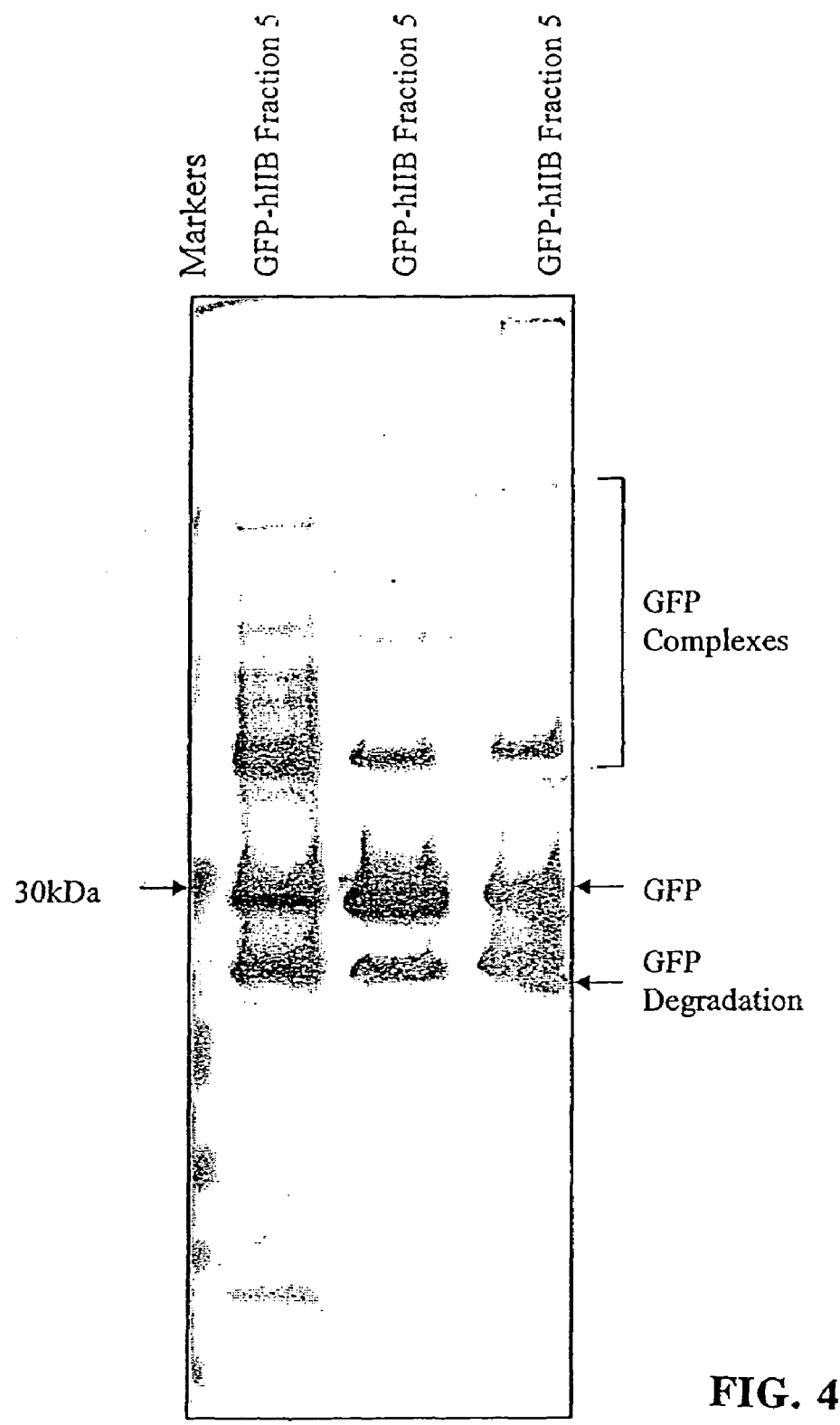
FIG. 4. Protein content of immunoaffinity column peak fractions. Western blot showing the reactivity of purified peptides with mAbs IIB8 and 1GFP63.

The soluble fraction was applied to a IIB8-Sepharose immunoaffinity column, washed with TEN buffer followed by a wash with TE+0.5 buffer, then eluted with TE buffer containing 0.75 M ammonium sulfate and 40% propylene glycol. Sodium dodecyl sulfate polyacrylamide gel electrophoresis (SDS-PAGE) analyses indicate that both hIIB and hIIBK2Q-tagged GFP can be purified in one chromatographic step using the IIB8-Sepharose column (FIG. 3). The column used to purify hIIB was also washed with TE containing 40% propylene glycol. Although additional proteins appear to purify along with the fusion proteins, Western blot analysis shows that all significant protein bands are GFP-related (see FIG. 4).

Figure 5:
FIG. 5. MonoQ anion-exchange chromatography on immunoaffinity column peak fractions. GFP-hIIBK2Q was eluted during 0–0.5 M NaCl salt gradient. The column was then washed with 1 M NaCl. The elution profile showed three peaks during the salt gradient (designated 9, 21, 28) and one peak in response to the 1 M NaCl wash (33). SDS-PAGE gel shows protein content of peak fractions 9 and 21. Peaks seen at 28 and 33 did not contain significant protein content.

To confirm that other proteins are not significantly contaminating the purification procedure, a MonoQ anion-exchange column was utilized to further separate the immunoaffinity column peak fractions. These fractions were diluted and loaded onto the MonoQ column, then eluted over a 0–0.5 M NaCl salt gradient. Finally, the column was washed with 1 M NaCl. Four peaks seen over the elution time were collected and analyzed by SDS-PAGE. Fraction 9 was extremely concentrated, as seen by the fluorescence under the UV light. Fractions 21, 28, and 33 were all further concentrated approximately 40-fold while the flowthrough was concentrated 160-fold prior to loading on the SDS-PAGE gel. The later peaks, 28 and 33, did not show any significant protein content (data not shown). SDS-PAGE gel showed that fraction 9 contained pure GFP and fraction 21 showed a few light protein bands (FIG. 5).

Figure 6:
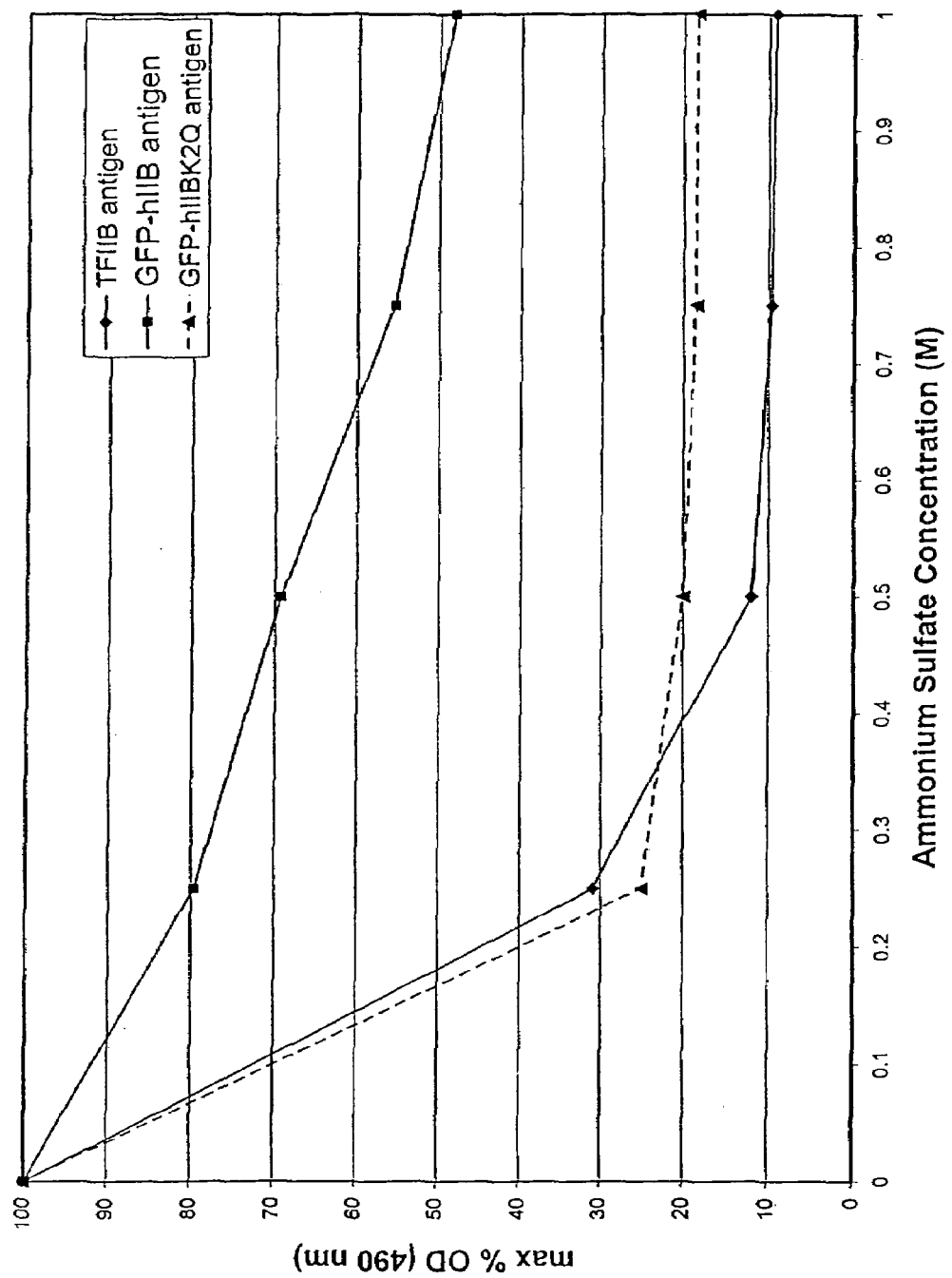
FIG. 6. ELISA-Elution assay to examine polyol-responsiveness of epitope-tagged GFP compared to human TFIIB. Different antigens (human TFIIB, GFP-hIIB, and GFP-hIIBK2Q) were tested for reactivity with mAb IIB8 after 20-minute incubation in elution buffer containing TE+40% propylene glycol+various concentrations of ammonium sulfate. GFP-hIIB did not respond to the elution buffer as well as TFIIB or GFP-hIIBK2Q.

Polyol-responsiveness of Epitope Tags: ELISA-elution assays were used to determine whether the epitope tags were as responsive to the elution buffer as the native protein. TFIIB, hIIB, and hIIBK2Q were tested with various concentrations of ammonium sulfate and propylene glycol. A reduction in signal in this assay indicates a disruption to the antibody-antigen interaction. Each protein showed a decrease in signal in response to the elution buffer. hIIBK2Q was more polyol-responsive than hIIB. A representative result is shown in FIG. 6.

Comparison of the Yeast and Human IIB8 Epitopes: Although the IIB8 epitope in human TFIIB has a very similar sequence in yeast, IIB8 does not recognize the endogenous protein in yeast on a Western blot (FIG. 7). The lack of mAb IIB8 reactivity to yeast TFIIB was surprising considering the yeast protein has the identical consensus sequence found by phage display. The epitope may refold better as a tag when compared to the full length protein resulting in different IIB8 reactivity. In order to find which difference in the homologous region is responsible for the lack of IIB8 affinity, two additional epitope tags were made incorporating the variations, hIIBK2D and yIIB. These tags were fused to the C-terminus of GFP. Each of these constructs reacted with IIB8 on a Western blot; however, the affinity of IIB8 for these tags was significantly lower compared to the human IIB8 epitope (FIG. 8). A summary of IIB8 epitopes and their activities is shown in Table 5.

TABLE 5

Summary of various IIB8 epitopes:

| Epitope | Sequence | Approximate Western Blot IIB8 Reactivity | Immunoaffinity Chromatography Efficiency |
|---|---|---|---|
| Human TFIIB | TKDPSRVG (SEQ. ID. NO: 24) | ++++ | ++++ |
| hIIB | TKDPSRVG (SEQ. ID. NO: 25) | ++++ | +++ |
| hIIBK2Q | TQDPSRVG (SEQ. ID. NO: 26) | ++++ | ++++ |
| hIIBK2D | TDDPSRVG (SEQ. ID. NO: 27) | + | [a]ND |
| yIIB | TGDDPSRVG (SEQ. ID. NO: 28) | + | [a]ND |
| Yeast TFIIB | TGDDPSRVG (SEQ. ID. NO: 29) | − | [a]ND |

[a]– not determined

Endogenous proteins as well as the four epitope tags designed are included. Reactivity of mAb IIB8 on a Western blot and purification efficiency through the IIB8-Sepharose column are approximated.

Example 2

In this Example, the epitope for the PR-mAb designated NT73 has been identified. This epitope reacts with the β' subunit of *E. coli* RNAP [7]. This Example demonstrates that the epitope can be used as an epitope tag to purify other proteins by the gentle polyol-elution method disclosed and claimed herein.

Reagents and Buffers: All chemicals were obtained from Sigma Chemical Co. (St Louis, Mo.) unless otherwise specified. Polyethyleneimine (PEI) was obtained from Aldrich (catalog no. 40, 872–7) and a 10% solution was prepared as described previously [31]. All restriction endonucleases were obtained from New England Biolabs (Beverly, Mass.) except for Nde I, which was obtained from Roche (Indianapolis, Ind.). Ligations were performed using the Rapid DNA Ligation kit from Roche, following the manufacturer's instructions. TE buffer contained 50 mM Tris-HCl, 0.1 mM EDTA, pH 7.9. TEN buffer was TE containing 100 mM NaCl. All pH values were determined at 23° C.

Antibodies: The production, purification, and use of mAb NT73 in immunoaffinity chromatography have been described [7]. The mAb NT73 itself can be obtained commercially from Neoclone (Madison, Wis.). The NT73 mAb and the control mAb (NT15) both react with the β' subunit of RNAP. The mAb IIB8 has also been described, and binds to an epitope contained within amino acids 52 to 105 of human transcription factor TFIIB [12]. The mAb 1GFP63 was prepared by conventional hybridoma methods, using splenocytes from a mouse that had been immunized with recombinant GFP purified from inclusion bodies by refolding with the detergent Sarkosyl (sodium lauroyl sarcosinate). Immunoadsorbents were prepared using cyanogen bromide-activated Sepharose 4B (Sigma) as previously described [3, 7]. All animal protocols were approved by the University of Wisconsin-Madison Medical School Animal Use and Care Committee.

Oligonucleotides and DNA Amplification and Sequencing: All oligonucleotides for recombinant DNA construction were synthesized by the University of Wisconsin Biotechnology Center. DNA was amplified with pfu polymerase (Stratagene, La Jolla, Calif.). All recombinant DNA constructions were sequenced at the McArdle Laboratory DNA Sequencing Facility using an ABI PRISM 373 DNA Sequencer (Applied Biosystems, Foster City, Calif.).

Plasmids: Plasmid pTA499, containing the gene for the β' subunit of E. coli RNAP with an N-terminal hexahistidine-tag ($His_6$-tag) contained in the pET28b vector, has been described [32]. Plasmid pTA500, contained β' with a C-terminal $His_6$-tag and has been described [32]. Plasmid phIIB, containing the gene for the human transcription factor IIB (TFIIB), has been described [11]. Plasmid TU#147, containing the gene for green fluorescent protein (GFP), was a gift from Martin Chalfie (Columbia University, New York, N.Y.); this plasmid contains the coding region for GFP sub-cloned from plasmid TU#58, previously described [33].

Protein Expression: Plasmids were transformed into E. coli BL21 (DE3)pLysS (Novagen, Madison, Wis.). Transformants were cultured in LB broth containing either 100 μg ampicillin/ml (pET11a vectors) or 30 μg kanamycin per ml (pET28b or pET33 vectors) and 35 μg chloramphenicol per ml. Cultures were induced at an O.D. (600 nm) of 0.6 with 1 mM isopropylthiogalactoside (IPTG) for 2.5 hr [14]. Cultures expressing the epitope-tagged version of GFP were grown and induced at 26° C. to increase the proportion of GFP that is soluble. Other cultures were grown and induced at 37° C.

SDS-PAGE and Western Blotting: Proteins were separated by electrophoresis by SDS-PAGE, using either 12% or 15% Tris-glycine polyacrylamide gels or 4–12% NuPAGE polyacrylamide gels (Invitrogen, Carlsbad, Calif.). Western blots were prepared as described previously [7], using a secondary antibody (anti-mouse IgG) that was conjugated to alkaline phosphatase and the 5-bromo-4-chloro-3-indolyl phosphate and nitro-blue tetrazolium (BCIP/NBT) reagent as substrate. For the Western blots containing the ordered-fragment ladders, the secondary antibody was conjugated to horseradish peroxidase and the substrate was the enhanced chemiluminescence (ECL) reagents from Amersham Biosciences (Piscataway, N.J.). Prestained molecular weight markers (SDS-7B, Sigma) were included on all gels; these markers were visible when transferred to the nitrocellulose.

Epitope Mapping of mAb NT73: The ordered fragment ladder method of epitope mapping has been described [34]. Briefly, the amino acid sequence of the β' subunit was analyzed by the MacVector Software package (Oxford Molecular Group) to determine which chemical or enzymatic cleavages would provide the most useful information. The β' subunit, containing either a N- or C-terminal $His_6$ tag, was expressed and recovered as insoluble inclusion body material. The inclusion body material was solublized with denaturants and chemically cleaved with either hydroxylamine or iodosobenzoic acid as described previously [32, 35]. The cleaved material was then bound to $Ni^{2+}$-NTA (Qiagen, Valencia, Calif.) under denaturing conditions to separate the fragments containing the $His_6$ tag from non-tagged fragments. The material that bound to the $Ni^{2+}$-NTA was then subjected to SDS-PAGE and Western blotting to determine the rough location of each epitope by the method of ordered-fragment ladder Western analysis [34, 35].

Deletion analysis was performed using a C-terminal peptide of β' and the Erase-a-Base kit from Promega (Madison, Wis.). The nucleotide sequences encoding amino acids 1027–1407 of the β' subunit were amplified from pTA499 by the polymerase chain reaction (PCR) using a forward primer containing a Nde I site followed by 15 nucleotides specific for the β' sequence to be amplified. The reverse primer contained 15 nucleotides specific to the last 5 codons of β' followed by two stop codons and a Bam HI site. The amplified DNA was cloned into the Nde I and Bam HI sites of pET33b (Novagen). This plasmid (10 μg) was digested with Sac I (in the vector) and Bam HI. The digested plasmid was then subjected to digestion by exonuclease. The reaction was controlled by incubation at 22° C. (removes about 80 bp/min), and samples were removed at 15-sec intervals. The DNA samples were processed according to manufacturer's protocol, and the ligated samples were transformed into E. coli JM109. Mini-prep DNA samples from transformants were sequenced to identify nested deletions from the C-terminus of the β' subunit.

Peptide tags were constructed by using complementary synthetic oligonucleotides containing the coding regions for overlapping peptides. Each pair of oligonucleotides contained a 5' Nco I site. The 3' end contained two translational stop codons followed by a Bam HI site. Oligonucleotides were designed to have the required sticky ends. Oligonucleotides were phosphorylated with polynucleotide kinase, mixed in equimolar proportions, and heated to 90° C. for 20 min in a heating block. The heating block was then allowed to return to room temperature (about 1 hr), and the annealed oligonucleotides were ligated into phIIB that had been digested with Nco I and Bam HI. Expression of this gene resulted in a soluble protein containing the peptide tag fused to the N-terminal domain of TFIIB. mAb IIB8 reacts with the N-terminal domain of TFIIB and was used as a control mAb for protein expression in Western blot assays.

Epitope tagging of GFP: The C-terminal epitope was added to GFP by using the complementary oligonucleotide method described above, except that oligonucleotides contained Bam HI sites on both ends. GFP was subcloned by amplifying the coding sequence from plasmid TU#147 by PCR, using primers containing Nhe I and Bam HI sites, and inserted into pET 11a. The annealed oligonucleotides were ligated into the Bam HI site, which resulted in fusing the epitope to the C-terminus of GFP. The construction resulted in the addition of a glycine residue between the C-terminus of GFP and the epitope. DNA sequencing confirmed that only one epitope was incorporated. The resulting fusion protein was [GFP]-GSLAELLNAGLGGS(SEQ.ID.NO:22), where the epitope tag is underlined.

The N-terminal epitope was added by ligating two complementary oligonucleotides containing the NT73 epitope into the Nhe I and Bam HI sites of pET11a. The coding region of GFP was then amplified from TU#147 by PCR, incorporating a Bam HI site on the 5' end and a Hind III site on the 3' end. This PCR product was then ligated into the Bam HI and Hind III sites of the plasmid containing the epitope tag. This construction resulted in the addition of two amino acids (glycine and serine) between the epitope and the GPF coding region. The resulting fusion protein was M SLAELLNAGLGGSGS-[GFP] (SEQ. ID. NO: 23), where the epitope tag is underlined.

ELISA-elution assays: ELISA-elution assays were performed as previously described [2, 3, 6, 7], using 50 ng of core RNAP or 30 ng of epitope-tagged GFP to coat each well. Briefly, NT73 was reacted with the immobilized antigen. After washing, the wells were treated with the elution buffer (TE containing combinations of propylene glycol and NaCl) for 20 min. The elution buffer was washed away, and the remaining NT73 was detected by the use of an enzyme-conjugated secondary antibody and appropriate substrate.

Purification of epitope-tagged proteins: Epitope-taggedGFP. A frozen cell pellet from 300 ml of induced culture (about 0.75 g wet weight) was resuspended in 10 ml of TEN buffer. Cells were lysed by sonication (5×30 s bursts on ice) and the cell debris and inclusion bodies were removed by centrifugation (30,000 g, 20 min, 4° C.). The soluble fraction was then applied directly to a 2 ml column of NT73-Sepharose. The column was washed with 10 volumes of TEN, followed by 3 volumes of TE containing 0.5 M NaCl. The epitope-tagged GFP was eluted with TE containing 0.7 M NaCl and 30% propylene glycol.

Epitope-tagged TFIIB N-terminal domain: The frozen cell pellet from 100 ml of induced culture (about 0.25 g wet weight) was resuspended in 8 ml of TEN and lysed by sonication as described hereinabove. The soluble fraction was adjusted to 0.5 M NaCl and treated with 0.2% polyethyleimine (PEI) as described [11]. The PEI precipitate was removed by centrifugation, and the supernatant fluid was applied to the NT73 -conjugated Sepharose.

Results and Significance of Example 2

Epitope mapping: The β' subunit of *E. coli* RNAP consists of 1407 amino acids and is one of the largest proteins in *E. coli*. An attempt to identify the epitope for mAb NT73 by phage display was not successful (unpublished data). Therefore, several approaches had to be combined in order to deal with the large β' protein, and yet identify the smallest epitope tag.

The rough location of the NT73 epitope was determined by the "ordered fragment ladder" method previously described [34, 35]. The ordered fragment ladder indicated that the NT73 epitope was located in the last 112 amino acids of the protein (FIG. 10A). Western blots showing the reactivity of mAbs NT73 and NT 15 with the ordered fragment ladders are shown in FIG. 10B. Mapping of the NT 15 epitope (located N-terminal of this region), provided a convenient control mAb for further mapping of the NT73 epitope by preparing deletions from the C-terminal end of the molecule. Therefore, the C-terminal portion (amino acids 1027–1407) of the molecule containing the epitopes for mAbs NT15 and NT73 was cloned and 3' deletions of the cloned gene fragment were prepared (FIG. 10A). Sequencing of the DNA, using the T7 terminator primer, indicated that a reasonable set of deletions had been obtained. However, when these truncated proteins were expressed and subjected to Western blotting, none of the truncated proteins reacted with NT73, but all of them reacted with NT15. A Western blot showing the reactivity of mAbs NT73 and NT15 with the C-terminal fragment and the fragment containing a deletion of the last 13 amino acids is shown in FIG. 10C. This indicated that at least part of the NT73 epitope was contained within the last 13 amino acids of the β' subunit.

To determine if these 13 amino acids constituted the epitope, a peptide tag containing only these thirteen amino acids (ep2 in FIG. 11A) was fused to a carrier protein. The N-terminus of human TFIIB was chosen, which is described in FIG. 11B. This construction resulted in a fusion protein of a convenient size that contained a known epitope for a control antibody (mAb IIB8), but was unrelated to the endogenous epitope-containing protein. However, the TFIIB fragment containing the 13 amino acid tag (ep2) did not react with NT73, although a peptide tag containing the last 16 amino acids of β' (ep5 in FIG. 11A) did react with NT73 (see FIG. 11C). Therefore, several overlapping peptide tags were constructed (summarized in FIG. 11A), and a tentative peptide tag containing the epitope with the sequence SLAELLNAGLGGS (SEQ. ID. NO: 1) was proposed.

Purification of epitope-tagged proteins: To determine if the epitope can function as a tag for the purification of proteins, the epitope was fused to either the N- or C-terminus of GFP, and the resulting fusion protein was expressed in *E. coli*. A Western blot showing the expression of the C-terminally epitope-tagged GFP (GFP-cep) is shown in FIG. 12A. Although the *E. coli* expression system is not ideal because of the endogenous epitope on the β' subunit in this organism, the goal was to determine the proof-of-principle of the polyol-responsive epitope tag in an easy-to-manipulate system. It was decided to use GFP because of its importance in many biological systems as a reporter protein [17]. In addition, the fluorescence of the GFP can be directly monitored to assess the activity of the protein after addition of the epitope and during the elution procedure.

Although GFP tends to form inclusion bodies when expressed in *E. coli*, some soluble protein can be obtained if the protein is expressed at 26° C. The GFP-cep seems to express better than the N-terminally tagged-GFP (GFP-nep) under these conditions, but the majority of the GFP-cep is recovered in the insoluble inclusion bodies (FIG. 12B).

The soluble fraction was applied to the NT73 column, washed with buffer containing 0.5 M NaCl, and then eluted with polyol-elution buffer containing 0.7 M NaCl and 30% propylene glycol. SDS-PAGE analyses of the fractions from the GFP-cep and GFP-nep purifications indicated that the tagged proteins can be purified in a single chromatographic step using NT73-Sepharose (see FIGS. 12B and 12C). A prominent, faster migrating protein (about 20 kDa) seemed to co-purify with the GFP. However, Western blot analysis using mAbs NT73 and 1GFP63 indicated that this major protein contaminant is a fragment of GFP, containing the C-terminal epitope tag (FIG. 12D). In addition, the Western blot detected some minor proteins that appear to be multimers of GFP which were not dissociated by the sample preparation. The β' RNAP subunit could also be detected at about 150 kDa.

To confirm the usefulness of this tag for protein purification, the NT73 column was used to purify the truncated form of the human transcription factor TFIIB that had been fused to the epitope (FIG. 11B). This domain of TFIIB remains soluble when expressed in E. coli at 37° C. The soluble fraction was adjusted to 0.5 M NaCl and treated with 0.2% PEI. Under these conditions, the PEI precipitates the nucleic acids and the endogenous RNAP [36]. The column was then washed with 0.5 M NaCl and eluted with TE buffer containing 0.7 M NaCl and 30% propylene glycol. The eluted fractions are shown on the SDS-PAGE gel in FIG. 13. This procedure yielded highly purified epitope-tagged protein.

Polyol-responsiveness of the epitope tag: To ensure that mAb NT73 has the same polyol-responsiveness toward the epitope tag as it does toward the epitope when it is contained in the native protein environment, the epitope-tagged GFP was tested in the ELISA-elution assays with different concentrations of propylene glycol and NaCl. In the ELISA-elution, a reduction of the signal indicates that the antigen-antibody interaction has been disrupted. The results are shown in FIGS. 14A and 14B. With minor experimental variability, the epitope-tagged GFP (FIG. 14A) showed the same response in the ELISA-elution assay to different combinations of NaCl and propylene glycol as did the core RNAP (FIG. 14B).

Significance of Example 2: The use of affinity tags for developing protein purification methods has been of considerable interest. Previously, PR-mAbs with the useful properties of having high affinity, but releasing antigen under nondenaturing conditions have been identified. However, to make this polyol-responsive immunoaffinity procedure more adaptable to other systems, the present inventors have (in this Example 2) identified the epitope for one of these mAbs and have demonstrated that it can be used as an epitope tag for the gentle purification of other proteins.

Many researchers use the $His_6$-tag for purification of proteins, but the polyol-responsive mAb tag provides an attractive alternative. Comparison of the NT73 immunoaffinity column with a Ni-NTA column for purification of E. coli RNAP showed that the immunoaffinity column yielded purer RNAP [16]. On one hand, the immunoaffinity column can be washed with either high salt or polyol separately to help reduce the nonspecifically bound proteins before the polyol/salt combination is used (data not shown). On the other hand, $Ni^{+2}$-NTA columns are always loaded at 0.5 M NaCl to prevent protein binding to the $Ni^{+2}$-NTA by ionic interactions. This high salt can lead to dissociation of some proteins from multisubunit protein complexes. In addition, the immunoaffinity column can be used when the target protein, or protein complex, contains a metal ion, which can be chelated by imidazole. While the cost of the mAb to generate the affinity resin is a disadvantage, efforts are underway to express this antibody as a single-chain variable fragment (scFv) that can be produced in bacteria.

The amino acid composition of the epitope was surprising. It contains only one charged residue and no bulky residues. Clearly, the epitope tag did not interfere with the fluorescence of the epitope-GFP, and it is unlikely that this epitope would interfere with the activity of other tagged proteins, and probably would not need to be cleaved off.

This Example shows that the epitope tag can be fused to either the N- or C-terminus of GFP. (Although, for reasons that are unclear, the N-terminally tagged-GFP does not express as well as the C-terminally tagged-protein.) While contaminating proteins seemed to be present on the SDS-PAGE analysis (see FIGS. 12B and 12C), Western blot analysis of the epitope-tagged GFP revealed that the other protein species recovered from the immunoaffinity chromatography were related to GFP (see FIG. 12D). This co-purification of GFP-fragments has been attributed to the propensity of GFP to form dimmers [17].

In this Example, the epitope-tagged proteins were expressed in E. coli. Because there is also an endogenous E. coli RNAP that contains the epitope, a small amount of RNAP was co-purified with the GFP (e.g., see FIG. 12C, lanes 3 and 4). However, the large amount of the epitope-tagged, over-expressed protein was able to compete for binding to the mAb (FIG. 12B). The RNAP can be removed by adjusting the NaCl of the lysate to 0.5 M and adding PEI before the immunoaffinity chromatography step (FIG. 13), provided that the target protein does not precipitate under these conditions. It has been determined that the far C-terminal domain of β' is not necessary for activity (Konstantin Severinov, personal communication). Therefore, it might be possible to delete the last 13 amino acids of the endogenous β', thereby creating a host strain whose RNAP will not bind to mAb NT73.

The epitope tag described in this Example is suitable for purifying proteins that are expressed in eukaryotic systems. Extracts made from yeast, HeLa cells, and insect cells have been tested using Western blots for reactivity with NT73. The mAb showed a slight reaction with one protein of about 100 kDa in HeLa cells and one of about 50 kDa in yeast (data not shown). Additionally, extracts prepared from Xenopus embryos did not react with mAb NT73 on Western blots (Michael Sheets, personal communication).

The fact that NT73 can recover RNAP from cell extracts (RNAP comprises only about 1% of the total protein in E. coli) suggests that the affinity of NT73 is quite high.

PR-mAbs are not associated with a particular subclass of IgG. PR-mAbs have been identified that are $IgG_1$ (like NT73), $IgG_{2a}$ or $IgG_{2b}$. PR-mAbs have also been identified that are IgM immunoglobulins, but these are less suitable for immunoaffinity chromatography because of their lower stability and their cumbersome purification procedures compared to IgG molecules.

As noted above, the ELISA-elution assay can lead to some false positive results. While not being limited to any underlying mechanism, it is believed that this is due to distortion of the antigen when it is immobilized on the polystyrene surface; this distortion probably exposes epitopes that are normally inaccessible to the antibody when it is in solution. The ELISA-elution assay has not yet been thoroughly tested for false-negative results because researchers are generally concerned with rescuing the positive hybridomas. A weak response to salt and polyol in the ELISA-elution assay does not necessarily result from high localized epitope concentration, leading to multivalent interactions with the antibody that would need to be disrupted simultaneously. For example, the PR-mAb designated 8WG16 reacts with the C-terminal heptapeptide repeat on the largest subunit of RNAP II. This sequence is repeated up to 52 times, depending upon the species. Yet, this mAb was the first PR-mAb identified by the ELISA-elution assay [6].

BIBLIOGRAPHY

[1] J. W. Jarvik, C. A. Telmer, Epitope tagging, Ann Rev Genet 32 (1998) 601–618.

[2] N. E. Thompson, R. R. Burgess, Immunoaffinity purification of RNA polymerase II and transcription factors using polyol-responsive monoclonal antibodies, Meth Enzymol 274 (1996) 513–26.

[3] N. E. Thompson, R. R. Burgess, Identification of polyol-responsive monoclonal antibodies for use in immunoaffinity chromatography, in: F. M. Ausubel et al. (Eds) Current protocols in molecular biology, Vol. 2, John Wiley & Sons Inc., New York, 2001, pp. 11.18.1.

[4] R. R. Burgess, N. E. Thompson, Advances in gentle immunoaffinity chromatography, Curr Opin. Biotechnol. 13 (2002) 304–308.

[5] A. M. Edwards, S. A. Darst, W. J. Feaver, N. E. Thompson, R. R. Burgess, R. D. Komberg, Purification and lipid-layer crystallization of yeast RNA polymerase II, Proc Natl Acad Sci USA 87 (1990) 2122–2126.

[6] N. E. Thompson, D. B. Aronson, R. R. Burgess, Purification of eukaryotic RNA polymerase II by immunoaffinity chromatography. Elution of active enzyme with protein stabilizing agents from a polyol-responsive monoclonal antibody, J Biol Chem 265 (1990) 7069–7077.

[7] N. E. Thompson, D. A. Hager, R. R. Burgess, Isolation and characterization of a polyol-responsive monoclonal antibody useful for gentle purification of *Escherichia coli* RNA polymerase, Biochemistry 31 (1992) 7003–7008.

[8] Y. Jiang, S. J. Zhang, S. M. Wu, M. Y. Lee, Immunoaffinity purification of DNA polymerase delta, Arch Biochem Biophys 320 (1995) 297–304.

[9] N. A. Lynch, H. Jiang, D. T. Gibson, Rapid purification of the oxygenase component of toluene di-oxygenase from a polyol-responsive monoclonal antibody, Appl Environ Microbiol 62 (1996) 2133–37.

[10] P. L. Nagy, J. Griesenbeck, R. D. Kornberg, M. L. Cleary, A trithorax-group complex purified from *Saccharomyces cerevisiae* is required for methylation of histone H3, Proc Natl Acad Sci USA 99 (2002) 90–94.

[11] N. E. Thompson, R. R. Burgess, Purification of recombinant human transcription factor IIB by immunoaffinity chromatography, Protein Exp Purif 5 (1994) 468–475.

[12] N. E. Thompson, L. A. Strasheim, K. M. Nolan, R. R. Burgess, Accessibility of epitopes on human transcription factor IIB in the native protein and in a complex with DNA, J Biol Chem 270 (1995) 4735–4740.

[13] N. E. Thompson, T. M. Arthur, R. R. Burgess, Development of an epitope tag for the gentle purification of proteins by immunoaffinity chromatography: application to epitope-tagged green fluorescent protein, Anal Biochem 323 (2003) 171–179.

[14] F. W. Studier, A. H. Rosenberg, J. J. Dunn, J. W. Dubendorff, Use of T7 RNA polymerase to direct expression of cloned genes, Meth Enzymol 185 (1990) 60–89.

[15] A. B. Sparks, N. B. Adey, S. Cwirla, B. K. Kay, Screening phage-displayed random peptide libraries, in B. K. Kay, J. Winter, and J. McCafferty (Eds.) Phage Display of Peptides and Proteins, Academic Press, San Diego, Calif., 1996, pp. 227–253.

[16] L. C. Anthony, R. R. Burgess, Conformational flexibility in sigma70 region 2 during transcription initiation, J. Biol. Chem. 277 (2002) 46433–46441.

[17] R. Y. Tsien, The green fluorescent protein, Ann Rev Biochem 67 (1998) 509–544.

[18] Subramanian A., Immunoaffinity chromatography, Mol Biotechnol 20 (2002) 41–47.

[19] Rhemrev-Boom M. M., Yates M, Rudolph M., and Raedts M., Immunoaffinity chromatography: a versatile tool for fast and selective purification, concentration, isolation and analysis, J Pharm & Biomed Anal, 24 (2001) 825–833.

[20] Weller, M. G., Immunochromatographic techniques—a critical review, Fresenius J Anal Chem, 366 (2000) 635–645.

[21] Hill C. L., Bartholomew R., Beidler D., and David G. S., "Switch" immunoaffinity chromatography with monoclonal antibodies, Biotechniques,1 (1983)14–17.

[22] Velander W. H., Orthner C. L., Thatakan J. P., Madurawe R. D., Ralston A. H., Strickland D. K., and Drohan W. N., Process implications for metal-dependent immunoaffinity interactions. Biotechnol Prog, 5 (1989) 119–125.

[23] Harlow E. and Lane D.: Antibodies: A Laboratory Manual. New York: Cold Spring Harbor Press, 1988.

[24] Largaespada D. A., Jackson M. W., Thompson N. E., Kaehler D. A., Byrd L. G., and Mushinski J. F., The ABL-MYC retrovirus generates antigen-specific plasmacytomas by in vitro infection of activated B-lymphocytes from spleen and other murine lymphoid organs. J Immunol Methods, 197 (1996) 85–95.

[25] See website for Neoclone, Inc., Madison, Wis.: www-.neoclone.com.

[26] Anthony, L. C. Foley, K. Thompson, N. and Burgess R. R. Expression, purification of, and monoclonal antibodies to the sigma factors from *E. coli*. Methods Enzymol., 370 (2003) 181–192.

[27] Bergendahl, V., Thompson, N. E., Foley, K., Olson, B., and Burgess, R. R. A cross-reactive polyol-responsive monoclonal antibody useful for isolation of core RNA polymerase from many bacterial species. Protein Expression Purification, 31(2003) 155–160.

[28] Duellman, S. J., Thompson, N. E. and Burgess, R. R. An epitope tag derived from human transcription factor IIB (TFIIB) that reacts with a polyol-responsive monoclonal antibody. Prot. Express. Purific. 35 (2004) 147–155.

[29] Thompson, N. E., Foley, K M, and Burgess, R. R. Antigen-binding properties of monoclonal antibodies reactive with human TATA-binding protein (TBP) and use in immunoaffinity chromatography. Prot. Express. Purific. In press, 2004.

[30] P. Cramer, D. A. Bushnell, J. Fu, A. L. Gnatt, B. Maier-Davis, N. E. Thompson, R. R. Burgess, A. M. Edwards, P. R. David. R. D. Kornberg, Architecture of RNA polymerase II and implications for the transcription mechanism, Science 288 (2000) 640–649.

[31] J. J. Jendrisak, R. R. Burgess, A new method for the large-scale purification of wheat germ RNA polymerase II, Biochemistry 14 (1975) 4639–4645.

[32] 14. T. M. Arthur, R R. Burgess, Localization of a sigma70 binding site on the N terminus of the *Escherichia coli* RNA polymerase b' subunit, J. Biol. Chem. 273 (1998) 31381–31387.

[33] 16. M. Chalfie, Y. Tu, G. Euskirchen, W. W. Ward, D. C. Prasher, Green fluorescent protein as a marker for gene expression, Science 263 (1994) 802–805.

[34] 18. L. Rao, D. P. Jones, L. H. Nguyen, S. A. McMahan, R. R. Burgess, Epitope mapping using histidine-tagged protein fragments: application to *Escherichia coli* RNA polymerase sigma 70, Anal. Biochem. 241 (1996) 173–179.

[35] 19. R. R. Burgess, T. M. Arthur, B. C. Pietz, Mapping protein-protein interaction domains using ordered fragment ladder far-western analysis of hexahistidine-tagged fusion proteins, Methods Enzymol. 328 (2000) 141–157.

[36] 21. R. R. Burgess, J. J. Jendrisak, A procedure for the rapid, large-scale purification of *Escherichia coli* DNA-dependent RNA polymerase involving Polymin P precipitation and DNA-cellulose chromatography, Biochemistry 21 (1975) 4634–4638.

What is claimed is:

1. A method of isolating, purifying, or concentrating a target compound, the method comprising:
   (a) conjugating the target compound to an epitope for a polyol-responsive monoclonal antibody (PR-mAb) to yield a conjugate, wherein the target compound is conjugated to an epitope consisting of the sequence selected from the group consisting of SLAELLNGLGGS (SEQ. ID. NO: 1). PTSPSYSPTSPSYS (SEQ. ID. NO: 2), TKDPSRVG (SEQ. ID. NO: 3) and TQDPSRVG (SEQ. ID. NO: 4); and then
   (b) contacting the conjugate of step (a) to an immunoaffinity matrix comprising a PR-mAb specifically reactive with the epitope of step (a).

2. The method of claim 1, wherein in step (a), the target compound is conjugated to the epitope via a linker.

3. The method of claim 2, wherein the linker is thermolabile, chemically labile, chemically cleavable, or a recognition/cleavage site for an enzyme.

4. The method of claim 2, wherein the linker comprises at least one amino acid residue.

5. The method of claim 2, wherein the linker comprises a recognition/cleavage site for a peptidase or protease.

6. The method of claim 2, wherein the linker comprises a recognition/cleavage site for a restriction endonuclease.

7. The method of claim 1, wherein in step (a), the target compound is conjugated directly to the epitope.

8. The method of claim 1, wherein in step (b), the inimunoaffinity matrix comprises a mammalian PR-mAb.

9. The method of claim 8, wherein in step (b), the immunoaffinity matrix comprises a murine PR-mAb.

10. A method of isolating, purifying, or concentrating a target polypeptide or protein, the method comprising:
    (a) providing a fusion protein comprising the target polypeptide or protein and an epitope for a PR-mAb, wherein the target polypeptide or protein is conjugated to an epitope selected from the group consisting of SLAELLNGLGGS (SEQ. ID. NO: 1), PTSPSYSPTSPSYS (SEQ. ID. NO: 2), TKDPSRVG (SEQ. ID. NO: 3) and TQDPSRVG (SEQ. ID. NO: 4); and then
    (b) contacting the fusion protein of step (a) to an immunoaffinity matrix comprising a PR-mAb specifically reactive with the epitope of step (a).

11. The method of claim 10, wherein in step (a), the fusion protein further comprises a linker disposed between the target polypeptide or protein and the epitope.

12. The method of claim 11, wherein the linker is thermolabile, chemically labile, or a recognition/cleavage site for an enzyme.

13. The method of claim 11, wherein the linker comprises at least one amino acid residue.

14. The method of claim 11, wherein the linker comprises a recognition/cleavage site for a peptidase or protease.

15. The method of claim 10, wherein in step (a), the target polypeptide or protein is fused directly to the epitope.

16. The method of claim 10, wherein in step (b), the irnmunoaffinity matrix comprises a mammalian PR-mAb.

17. The method of claim 16, wherein in step (b), the inimunoaffinity matrix comprises a murine PR-mAb.

18. A method of isolating, purifying, or concentrating a target compound, the method comprising:
    (a) conjugating a probe compound capable of binding to the target compound to an epitope for a polyol-responsive monoclonal antibody (PR-mAb) to yield a conjugate, wherein the probe compound is conjugated to an epitope consisting of the sequence selected from the group consisting of SLAELLNGLGGS (SEQ. ID. NO: 1). PTSPSYSPTSPSYS (SEQ. ID. NO: 2), TKDPSRVG (SEQ. ID. NO: 3) and TQDPSRVG (SEQ. ID. NO: 4); and then
    (b) contacting the conjugate of step (a) to a sample suspected of containing the target compound under conditions and for a time sufficient to allow the target compound to bind to the probe, thereby yielding a probe/target mixture;
    (c) contacting the probe/target mixture of step (b) to an immunoaffinity matrix comprising a PR-mAb specifically reactive with the epitope of step (a).

19. The method of claim 18, wherein in step (a), the probe compound is conjugated to the epitope via a linker.

20. The method of claim 19, wherein the linker is thermolabile, chemically labile, chemically cleavable, or a recognitionlcleavage site for an enzyme.

21. The method of claim 19, wherein the linker comprises at least one amino acid residue.

22. The method of claim 19, wherein the linker comprises a recognition/cleavage site for a peptidase or protease.

23. The method of claim 19, wherein the linker comprises a recognition/cleavage site for a restriction endonuclease.

24. The method of claim 18, wherein in step (a), the probe compound is conjugated directly to the epitope.

25. The method of claim 18, wherein in step (c), the inunumoaffinity matrix comprises a mammalian PR-mAb.

26. The method of claim 25, wherein in step (c), the inimunoaffmity matrix comprises a murine PR-mAb.

27. A composition of matter comprising: a target compound conjugated to an isolated polypeptide consisting of the amino acid sequence selected from the group consisting of SLAELLNGLGGS (SEQ. ID. NO: 1), PTSPSYSPTSPSYS (SEQ. ID. NO: 2), TKDPSRVG (SEQ. ID. NO: 3), and TQDPSRVG (SEQ. ID. NO: 4).

28. A composition of matter comprising: a target compound, a linker, and an isolated polypeptide, wherein the target compound is conjugated to the linker, and the linker is conjugated to the isolated polypeptide consisting of the amino acid sequence selected from the group consisting of SLAELLNGLGGS (SEQ. ID. NO: 1), PTSPSYSPTSPSYS (SEQ. ID. NO: 2), TKDPSRVG (SEQ. ID. NO: 3), and TQDPSRVG (SEQ. ID. NO: 4).

29. An isolated polypeptide consisting of the to amino acid sequence selected from the group consisting of SLAELLNGLGGS (SEQ. ID. NO: 1), PTSPSYSPTSPSYS (SEQ. ID. NO: 2), TKDPSRVG (SEQ. ID. NO: 3), and TQDPSRVG (SEQ. ID. NO: 4).

* * * * *

UNITED STATES PATENT AND TRADEMARK OFFICE
CERTIFICATE OF CORRECTION

PATENT NO. : 7,241,580 B2
APPLICATION NO. : 11/148074
DATED : July 10, 2007
INVENTOR(S) : Duellman et al.

It is certified that error appears in the above-identified patent and that said Letters Patent is hereby corrected as shown below:

Claim 1, Column 39, Line 20: Delete the word "and".

Claim 8, Column 39, Line 38: Delete "inimunoaffinity" and substitute therefor -- immunoaffinity -- .

Claim 10, Column 39, Line 49: Delete the word "and".

Claim 16, Column 39, Line 67: Delete "irnmunoaffinity" and substitute therefor -- immunoaffinity --.

Claim 17, Column 40, Line 11: Delete "inimunoaffinity" and substitute therefor -- immunoaffinity --.

Claim 20, Column 40, Lines 33-34: Delete: "rec-ognitionlcleavage" and substitute therefor -- recognition/cleavage --.

Claim 25, Column 40, Line 44: Delete: "inununoaffinity" and substitute therefor -- immunoaffinity --.

Claim 26, Column 40, Line 46: Delete: "inimunoaffmity" and substitute therefor -- inimunoaffinity --.

UNITED STATES PATENT AND TRADEMARK OFFICE
CERTIFICATE OF CORRECTION

PATENT NO. : 7,241,580 B2
APPLICATION NO. : 11/148074
DATED : July 10, 2007
INVENTOR(S) : Duellman et al.

It is certified that error appears in the above-identified patent and that said Letters Patent is hereby corrected as shown below:

Claim 29, Column 40, Line 61: Delete the word "to".

Signed and Sealed this

Thirteenth Day of November, 2007

JON W. DUDAS
*Director of the United States Patent and Trademark Office*

UNITED STATES PATENT AND TRADEMARK OFFICE
CERTIFICATE OF CORRECTION

PATENT NO. : 7,241,580 B2  
APPLICATION NO. : 11/148074  
DATED : July 10, 2007  
INVENTOR(S) : Sarah J. Duellman et al.

Page 1 of 1

It is certified that error appears in the above-identified patent and that said Letters Patent is hereby corrected as shown below:

In the Specification

Column 1, Lines 15-17:
Delete the phrase:
"This work was made with United States government support awarded by the following agencies: NIH CA060896. United States has certain rights in this invention."
And replace with:
--This invention was made with government support under CA060896 awarded by the National Institutes of Health. The government has certain rights in the invention.--.

Signed and Sealed this  
Eighth Day of December, 2020

Andrei Iancu  
*Director of the United States Patent and Trademark Office*